United States Patent [19]

Nakayama et al.

[11] Patent Number: 6,083,187

[45] Date of Patent: Jul. 4, 2000

[54] METHOD AND APPARATUS FOR TREATING BLOOD

[75] Inventors: Takehisa Nakayama, Hyogo; Hiroshi Tachibana, Shiga; Eiichi Yoshida; Yasufumi Hamanishi, both of Hyogo; Yoshizumi Takao; Masataka Narisada, both of Tokyo, all of Japan

[73] Assignee: Kaneka Corporation, Osaka, Japan

[21] Appl. No.: 08/924,942

[22] Filed: Sep. 8, 1997

[30] Foreign Application Priority Data

| Sep. 9, 1996 | [JP] | Japan | 8-237438 |
| Sep. 9, 1996 | [JP] | Japan | 8-237439 |
| Sep. 9, 1996 | [JP] | Japan | 8-237440 |
| Sep. 9, 1996 | [JP] | Japan | 8-237441 |

[51] Int. Cl.$^7$ .......................... A61M 37/00; A61K 35/16; B01D 21/24
[52] U.S. Cl. .................................. 604/6; 604/4; 424/530; 210/98
[58] Field of Search ............................... 424/530; 604/4; 210/416.1, 97, 98; 222/401, 402.11

[56] References Cited

U.S. PATENT DOCUMENTS

| 5,098,372 | 3/1992 | Jonsson | 604/5 |
| 5,178,603 | 1/1993 | Prince | 604/6 |
| 5,318,512 | 6/1994 | Neumann | 604/6 |
| 5,391,142 | 2/1995 | Sites et al. | 604/4 |
| 5,403,272 | 4/1995 | Deniega et al. | 604/4 |
| 5,536,412 | 7/1996 | Ash | 210/645 |
| 5,695,653 | 12/1997 | Gsell et al. | 210/767 |
| 5,738,644 | 4/1998 | Holmes et al. | 604/4 |
| 5,753,227 | 5/1998 | Strahilevitz | 424/140.1 |
| 5,795,317 | 8/1998 | Brierton et al. | 604/5 |
| 5,813,842 | 9/1998 | Tamari | 417/477.1 |

Primary Examiner—Mark O. Polutta
Assistant Examiner—Patricia M. Bianco
Attorney, Agent, or Firm—Armstrong, Westerman, Hattori, McLeland, & Naughton

[57] ABSTRACT

The invention pertains to a method and apparatus for treating blood. If pressure constraints occur during the execution of blood treatment, the pump flow rates are rapidly decelerated to remove the pressure constraints so that the treating operation will restore the normal state as quickly as possible. After the pressure constraints have been removed, the pump flow rates are restored at a preset acceleration without causing any excessive pressure buildup due to an abruptly increased load. If the pump flow rates immediately after the start of operation of the processor are increased through two stages of acceleration, the target flow rates can be rapidly reached without exerting any abrupt load on the processor and, hence, without causing an excessive pressure buildup.

1 Claim, 11 Drawing Sheets

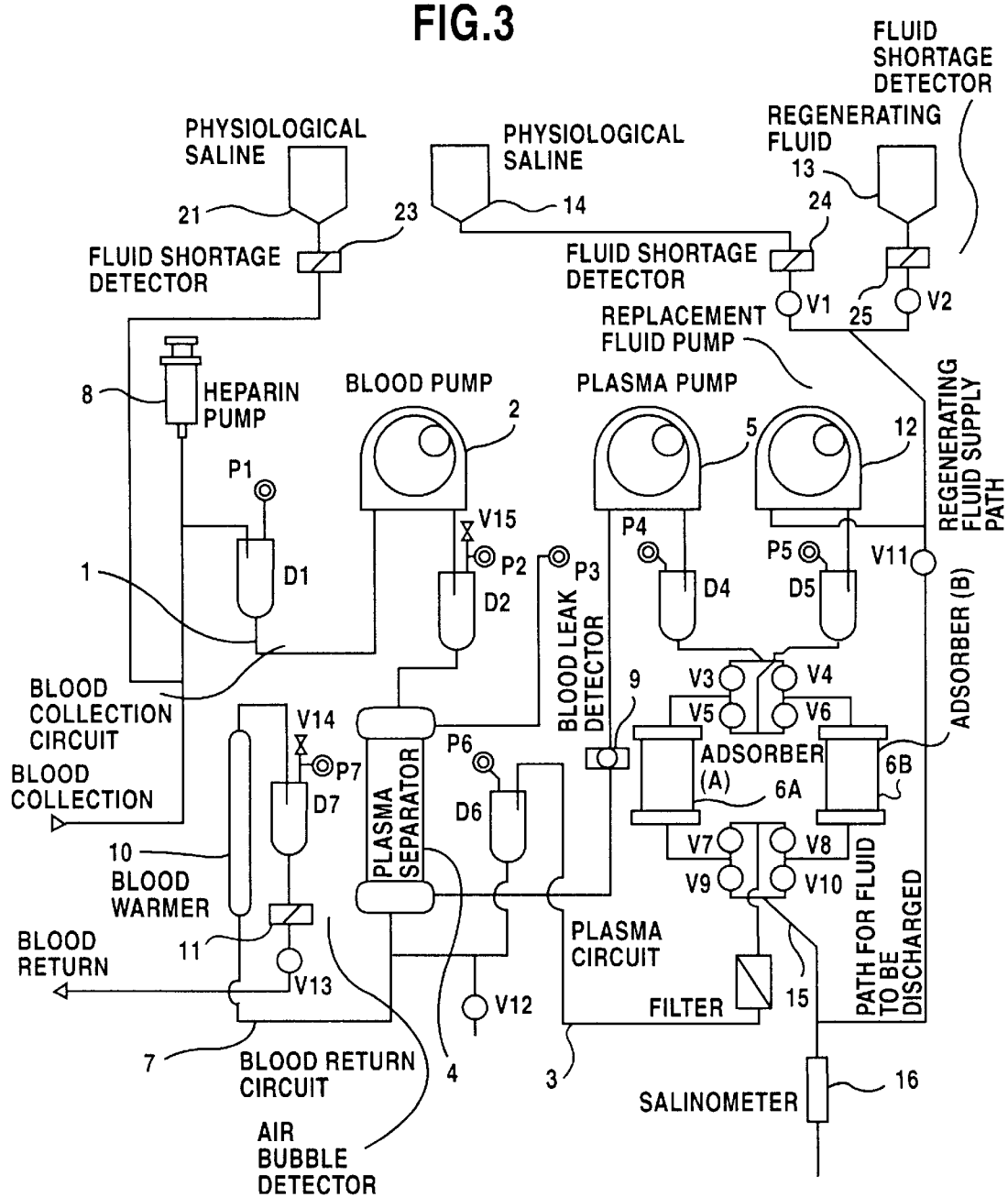

METHOD AND APPARATUS FOR TREATING BLOOD

BACKGROUND OF THE INVENTION

The present invention relates to a method and an apparatus for treating blood in various ways such as removing impurities and deleterious matter, and replacement of specific components.

For the treatment of various diseases, blood is treated in various ways, among which the following are conventionally known: a method in which plasma is separated from a blood sample and loaded on an adsorption column to remove the unwanted or deleterious matter by adsorption; plasma exchange in which the separated plasma is replaced by a replenishing fluid; double filtration for removing higher molecular weight components of the plasma; and artificial dialysis in which the blood sample is brought into contact with a semipermeable membrane.

These blood treating methods are implemented with an apparatus of blood treatment which generally comprises a cascade connection of a collection circuit for withdrawing a blood sample by means of a blood pump, a treating circuit for performing specified treatment on the blood sample and a return circuit through which the treated blood sample is returned to the patient. In addition, a heparin pump, a filter, a blood warmer, an air bubble detector, as well as a plurality of pressure gauges and clamp valves are provided at appropriate sites in the respective circuits. If the apparatus is a type that treats a separated plasma component of blood, a plasma separator, a plasma pump, a blood leak detector, an adsorber or a secondary filter and the like are also provided in the treatment circuit.

The apparatus of blood treatment having the construction described above is usually provided with control means for controlling the driving of the pumps and the opening/closing of the clamp valves such that the blood treatment can be accomplished by automated operation of the apparatus.

If any abnormality occurs to the pressures in the circuits or to devices in the apparatus of blood treatment during its use, the operation of the pumps has to be controlled in an appropriate way depending on the nature of the abnormality. According to Examined Japanese Patent Publications Nos. 28981/1990 and 50304/1993, if the blood withdrawing portion of an apparatus of blood treatment becomes constricted during treatment to produce a great negative pressure in the primary flow channel to the first pump, a further increase in the negative pressure can be avoided by reducing the rotating speeds of the first and second pumps while keeping the ratio between their flow rates constant.

This method is capable of dealing with the increase in negative pressure that occurs in the primary flow channel to the first pump on account of the constriction of the blood withdrawing portion of the apparatus of blood treatment. However, neither of the patents mentioned above discloses a technique for controlling the pumps when other abnormal events occur and while the operation restores the normal state.

SUMMARY OF THE INVENTION

The present invention provides a technique for achieving safe and efficient blood treatment by controlling the operational state of pumps in an appropriate way when starting the execution of blood treatment, when an abnormal event occurs during the execution of the treatment and while the operation restores the normal state.

The apparatus of blood treatment to be used in the invention comprises a collection circuit into which a blood sample is withdrawn by means of a blood pump, a treating circuit for performing specified treatment on the withdrawn blood sample and a return circuit through which the treated blood sample is returned to the patient, with pressure gauges being provided at appropriate sites in the collection, treating and return circuits. The apparatus of blood treatment also includes means for controlling the operation of the blood pump. The present invention is characterized by performing the following steps with the thus constructed apparatus of blood treatment.

(1) At the start of the treatment, the blood pump starts to operate and continues to run with the blood flow rate being increased at a preset normal acceleration until a specified target blood flow rate is reached; alternatively, the blood pump may be set in such a way that the blood flow rate is increased through at least two stages of acceleration, one being at a preset initial acceleration and the other at the normal acceleration.

(2) Once the blood pump flow rate has reached the target blood flow rate, the operation of the pump is controlled so as to maintain said target blood flow rate thereafter.

(3) If the values of pressure as detected by specified pressure gauges or the values calculated on said pressure gauges deviate from respective limiting values to cause pressure constraints, the blood pump flow rate is reduced at a specified deceleration.

(4) If the pressure constraints are removed, the blood pump flow rate is increased at the normal acceleration so that it is reverted toward the target blood flow rate.

The following step may additionally be performed.

(5) If any abnormal event other than the pressure constraints occurs during the operation of the blood pump, the blood pump flow rate is reduced at a specified deceleration and thereafter maintained at a standby flow rate not exceeding a preset limiting value.

The present invention can be applied to any blood treating methods including adsorptive removal, plasma exchange, double filtration and artificial dialysis.

BRIEF DESCRIPTION OF THE DRAWINGS

FIG. 3 is a diagram showing schematically the configuration of circuits in an apparatus of plasma treatment according to a second embodiment of the invention;

DETAILED DESCRIPTION OF THE PREFERRED EMBODIMENTS

Embodiments of the present invention will now be described with reference to the case where it is applied to an adsorptive blood treatment in which plasma is separated from a blood sample and freed of cholesterol by means of an adsorber.

Figure 1:
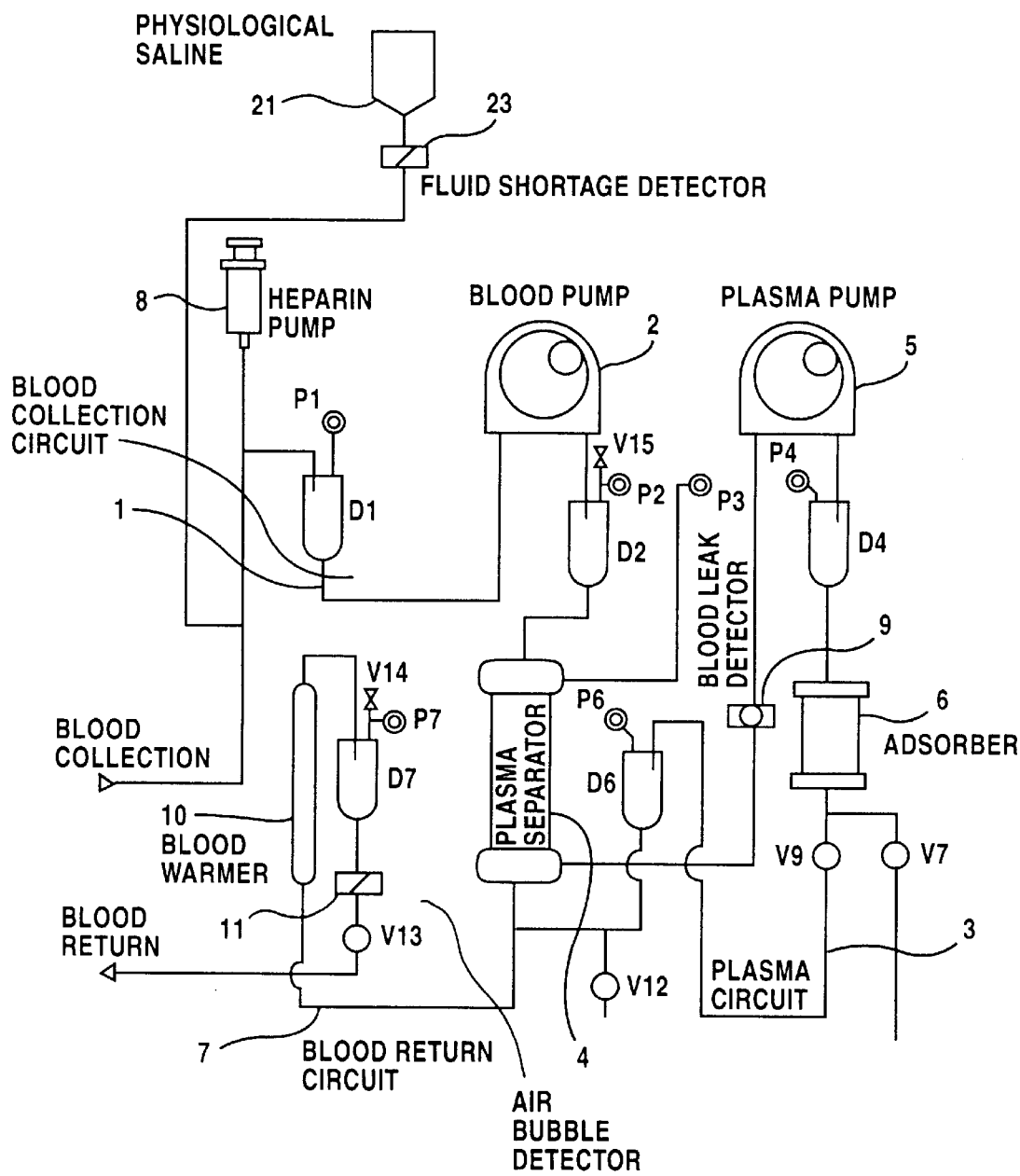
FIG. 1 is a diagram showing schematically the configuration of circuits in an apparatus of plasma treatment according to a first embodiment of the invention.

FIG. 1 shows an example of the apparatus of blood treatment for use in such adsorptive blood treatment. The apparatus comprises basically a collection circuit 1 for withdrawing a blood sample and supplying it into a plasma separator by means of a blood pump 2, a treating circuit or plasma circuit 3 in which the plasma separated from the blood sample by means of a plasma separator 4 is directed into a plasma pump 5, where it is freed of the unwanted cholesterol in an absorber 6, and a return circuit 7 in which the treated plasma is combined with the blood permeate from the plasma separator 4 and then returned to the patient.

Provided at appropriate sites in the circuits are a pressure gauge P3, drip chambers D1, D2, D4, D6 and D7 fitted with pressure gauges P1, P2, P4, P6 and P7, as well as flow channel controlling clamp valves V7, V9, V12, V13, V14 and V15. Also provided are an infuser 8 of anticoagulant heparin, a blood leak detector 9 for detecting the leakage of blood into the plasma emerging from the plasma separator 4, a blood warmer 10 for warming the returning blood to a specified temperature, an air bubble detector 11 for detecting the entrance of air bubbles into the returning blood, and any other necessary devices. An infuser of physiological saline 21 and a fluid shortage detector 23 are also provided.

The operation of the blood pump 2 and plasma pump 5, as well as the opening/closing of the clamp valves V7, V9, V12, V13, V14 and V15 are controlled by control means (not represented on the figures) including a CPU, a blood flow rate setting device and a plasma flow ratio setting device on the basis of such information as detection signals from the associated machine parts and the pressure gauges.

The clamp valves are ON/OFF controlled in operative association with the pumps to switch one flow channel to another in each of the steps involved, such as preparatory steps for setting up the circuits and rinsing their interiors with physiological saline prior to the start of blood treatment, the step of introducing a blood sample into the circuits so that it is subjected to plasma treatment with an adsorber and the step of recovering the residual blood in the circuits after the treatment. The control means controls the opening/closing of the clamp valves so as to form an appropriate flow channel for each of these steps.

The method of treating blood with the above-described apparatus of blood treatment is outlined below. In the following description, the pressures measured with the pressure gauges P1, P2 . . . are designated P1, P2 . . . , respectively, for the sake of convenience.

The blood treating steps will generally proceed in the following way. Usually, the execution of blood treatment is preceded by the preparatory steps of setting up the respective circuits and rinsing their interior with physiological saline. When the required preparatory steps end, the blood pump 2 is started to run so that a blood sample is withdrawn into the collection circuit 1 through a collection tip and thence supplied into the plasma separator 4. The plasma separated from the blood in the plasma separator 4 is forced by means of the plasma pump 5 through the (plasma) treating circuit 3 to be directed into the adsorber 6. As it passes through the adsorber 6, the plasma makes contact with the adsorbent in the adsorber 6, whereby the unwanted cholesterol is removed from the plasma. The treated plasma emerging from the adsorber 6 is combined with the blood permeate from the plasma separator 4 and returned to the patient through the return circuit 7. When the necessary treatment has been performed in this way, physiological saline is introduced into the circuits such that the residual blood and plasma are recovered from the circuits and returned to the patient.

In these blood treating steps, the operation of the blood pump 2 is controlled in such a way that the monitored values of a blood collection pressure P1, a venous blood pressure P7 and a differential pressure across the plasma separator $\Delta P2/6$ $(=P2-P6)$ will not exceed the limits of the respective values. If it is found that none of the monitored values have caused pressure constraints after the start of pump operation, the blood pump flow rate QB is increased at a preset initial acceleration $Vb_0$ until the integrated blood flow reaches a specified value, which is typically set to be approximately equal to the sum of the capacities of the collection circuit and the plasma separator.

When the integrated blood flow has reached the specified value, the initial acceleration $Vb_0$ of the blood pump flow rate is changed to the normal acceleration $Vb_1$ and the pump operation is continued until the desired target blood flow rate Qbs is reached. After QBs is reached, the operation of the blood pump 2 is controlled so as to maintain said target blood flow rate.

In order to ensure that an abrupt load is not exerted on a treating device such as the plasma separator 4 to cause an excessive pressure buildup, the initial acceleration $Vb_0$ is usually set at a lower value than the normal acceleration $Vb_1$. However, this is not always the case and depending on the specific situation of the treatment, $Vb_0$ may be set to be greater than $Vb_1$.

If the pressure values of P1, P2 and $\Delta P2/6$ being monitored with the associated pressure gauges deviate from the respective limiting values to cause pressure constraints, the blood pump flow rate is reduced at a specified deceleration $Vb_2$, which is set at a sufficiently great value to ensure that the pressure constraints can be removed rapidly. If the pressure constraints are removed, the blood pump flow rate is increased at the normal acceleration $Vb_1$ until the target blood flow rate QBs is restored.

Thus, in the present invention, if pressure constraints are exerted, the blood pump flow rate is reduced at a comparatively large deceleration, thereby allowing for rapid restoration of the machine operation from the abnormal pressure state. During the restoration, the blood flow rate is increased mildly enough to avoid the excessive pressure buildup due to an abruptly increasing load and this enables the blood pump 2 to be operated for a prolonged period without undergoing any constraints.

Even if the blood pump is controlled to maintain the target blood flow rate QBs, abnormal events other than the above-described pressure constraints may occur, as exemplified by abnormal pressure values detected by pressure gauges other than P1, P2 and P6, or the abnormal operation of certain valves. In this case, the blood pump flow rate may be decelerated momentarily at a sufficiently great deceleration $Vb_3$ to cause a drop to a standby flow rate QBa, which is maintained until the machine operation corrects the abnormal state. The standby flow rate QBa is set at a value that is lower than a preset upper limit but not so low as to cause blood coagulation in the circuits.

Figure 2A:
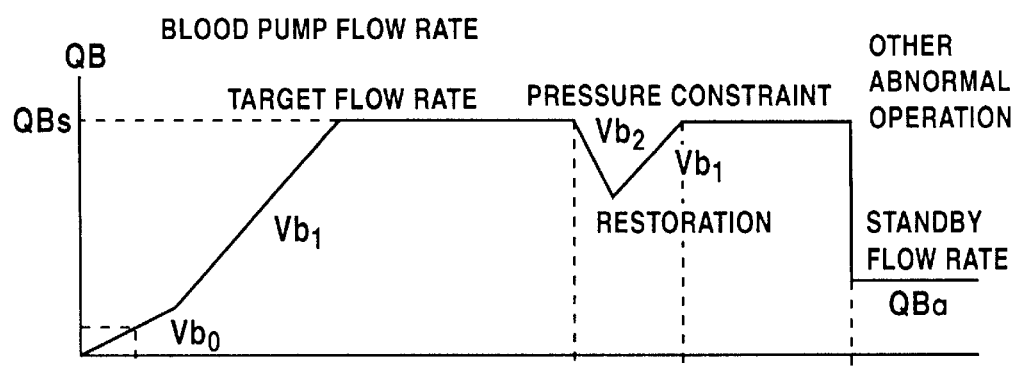
FIGS. 2A and 2B are graphs showing how various pumps are controlled in the plasma treating method of the invention.
Figure 2B:
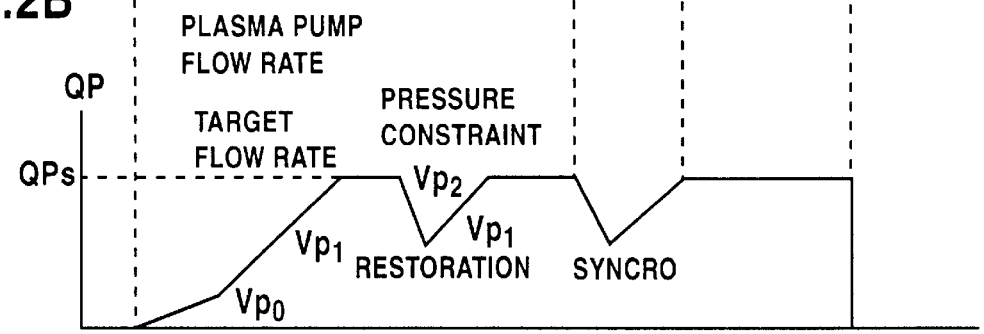

The above-described procedure of controlling the blood pump flow is illustrated by a timing chart in FIG. 2A, and FIG. 2B shows the procedure of controlling the plasma pump flow.

Referring now to the plasma pump 5, it remains at rest as long as the blood pump flow rate QB is below a prescribed value after the blood pump 2 started to run. If the plasma pump 5 is actuated simultaneously with the blood pump 2, the force to extract plasma will develop before the blood sample is fed into the plasma separator 4 and an extra load is imposed on machine parts. In order to prevent this difficulty, a certain time lag is provided before the plasma pump 5 is actuated.

When the blood pump flow rate QB has reached the prescribed value, the plasma pump 5 is started and controlled in such a way that the monitored values of TMP $[=(P2+P6)/2-P3]$ which represents the pressure difference across the separation membrane in the plasma separator 4 and $\Delta P4/6$ (=P4-P6) representing the pressure difference across the adsorber 6 will not exceed the respective limiting values. If no such pressure constraints are experienced by the plasma pump 5 after the start of its operation, the plasma pump flow rate QP is increased at a preset initial acceleration $Vp_0$ until the integrated flow reaches a specified value. When the integrated flow has reached the specified value, the initial acceleration $Vp_0$ is switched to a normal acceleration $Vp_1$ and the plasma pump flow rate QP is increased until it reaches the target plasma flow rate QPs.

The target plasma flow rate QPs is given as a function of QB (=the blood pump flow rate) and TMP (=the pressure difference across the separation membrane in the plasma separator 4). In other words, the plasma pump 5 is controlled to attain the target plasma flow rate QPs which is calculated at every moment on the basis of both the ratio determined from TMP and the actual value of blood pump flow rate QB. The value of integrated plasma flow at which the initial acceleration $Vp_0$ is switched to the normal acceleration $Vp_1$ is determined on the basis of the capacity of the secondary side (plasma volume) of the plasma separator 4.

In order to ensure that an abrupt load is not exerted on the separation membrane in the plasma separator 4 to cause an excessive pressure buildup, the initial acceleration $Vp_0$ is usually set at a lower value than the normal acceleration $Vp_1$. However, this is not always the case and depending on the specific situation of the processing, $Vp_0$ may be set to be greater than $Vp_1$.

If the values of pressures TMP and $\Delta P4/6$ being monitored with the associated pressure gauges deviate from the respective limiting values to cause pressure constraints, the plasma pump flow rate QP is reduced at a specified deceleration $Vp_2$, which is set at a sufficiently great value to ensure that the pressure constraints can be removed rapidly.

If the pressure constraints are removed, the plasma pump flow rate QP is increased at the normal acceleration $Vp_1$ such that it is reverted to the target plasma flow QPs.

Thus, in the present invention, if pressure constraints are exerted, pump flows are reduced at comparatively large decelerations, thereby allowing for rapid restoration of the machine operation from the abnormal pressure states. During the restoration phase, the pump flows are increased mildly enough to avoid the excessive pressure buildup due to an abruptly increasing load and this enables the pumps to be operated for a prolonged period without undergoing any constraints.

If the blood pump flow is to be reduced due to pressure constraints while the plasma pump is running normally, the plasma pump flow rate QP is reduced synchronously. In this case, the plasma pump flow rate QP is determined on the basis of blood pump flow rate QB by the same technique as employed to calculate the target plasma flow rate QPs. It should, however, be noted that if the blood pump flow rate QB becomes lower than the prescribed value, the plasma pump 5 is brought to a stop.

The above-described procedures of controlling the pump flows are illustrated by timing charts in FIGS. 2A and 2B.

The foregoing discussion is directed to the case of applying the present invention to the processing of a blood sample such that the unwanted matter is removed from plasma by means of an adsorber. This is not the sole applicable case of the invention and it may be applied to other blood treating methods including the double filtration of plasma, plasma exchange and artificial dialysis. If the invention is to be applied to these cases, the procedure of controlling the blood pump operation suffices to be modified in accordance with the specific embodiment of a respective blood treating method.

An example of the method of setting conditions for executing the plasma treating steps by means of the apparatus of plasma treatment shown in FIG. 1 will now be described below.

Immediately after the start of operation of the blood pump 2, the blood flow rate QB is increased at the initial acceleration $Vp_0$ which is set at an appropriate value within the range of 20 to 100 mL/min/min. When the integrated blood flow has reached 300 mL which is approximately equal to the sum of the capacities of the collection circuit 1 and the plasma separator 4, the initial acceleration $Vp_0$ is switched to the normal acceleration $Vp_1$ which is set at an appropriate value within the range of 20 to 150 mL/min/min and the blood pump flow rate is increased until the target blood flow rate QBs (=100 mL/min) is reached. The initial acceleration Vb is typically set to be smaller than the normal acceleration $Vp_1$ but this is not always the case of the invention. When the blood flow rate has reached the target value QBs, the operation of the blood pump 2 is controlled so as to maintain QBs.

The operation of the blood pump 2 is controlled in such a way that the monitored values of the blood collection pressure P1, the venous blood pressure P7 and the pressure difference across the plasma separator $\Delta P2/6$ will not exceed the limits of the respective values. If either one of said pressures deviates from the associated limiting value to cause a pressure constraint, namely, if P1 becomes lower than the lower limit, or if P7 exceeds the upper limit, or if $\Delta P2/6$ becomes greater than the upper limit, the blood pump flow rate QB is rapidly reduced at a sufficiently great deceleration of $Vp_2$ (=300 mL/min/min) to ensure that the pressure constraint is removed as soon as possible. When the pressure constraint is removed, the blood pump flow rate QB is increased again at the normal acceleration $Vp_1$ such that it is reverted toward the target blood flow rate QBs (=100 mL/min).

If there occurs any abnormal event other than the pressure constraints, as exemplified by abnormal operation of valves, and yet the blood pump 2 is running without trouble, the blood pump flow rate QB is rapidly decelerated to the standby flow rate QBa ($\leq 50$ mL/min) which is preset by a blood flow rate setting device and the blood circulation is continued by controlling the blood pump 2 such as to maintain QBa. If the abnormal event under consideration is removed, QB is reverted toward the target value QBs. The procedure of executing the restoration of QBs has already been described above.

Referring now to the plasma pump 5, it remains at rest until after the blood pump 2 has run to attain a QB value of 15 mL/min. When QB has reached 15 mL/min, the plasma pump is started to run with TMP [=(P2+P6)/2−P3= the pressure difference across the separation membrane in the plasma separator] and $\Delta$P4/6 (=P4−P6= the pressure difference across the adsorber 6) being monitored. Until after the integrated plasma flow has reached 50 mL which is approximately equal to the volume of plasma on the secondary side of the plasma separator 4, the plasma pump flow rate QP is increased at an initial acceleration of $Vp_0$ which is set within the range of 10 to 60 mL/min/min. Once the integrated plasma flow has reached 50 mL, the plasma pump flow rate QP is increased at a normal acceleration $Vp_1$ (10 to 100 mL/min/min) until it reaches the target plasma flow rate QPs. In order to ensure that the load on the machine parts will increase mildly, the normal acceleration $Vp_1$ is usually set to be greater than the initial acceleration $Vp_0$.

The plasma pump 5 is controlled at every moment such as to maintain the target plasma flow rate QPs which is calculated on the basis of QB and TMP.

The target plasma flow rate QPs is expressed as QPs= K·R1·QB, where QB is the blood pump flow rate, K is a coefficient of plasma flow ratio which is preset by a plasma flow ratio setting device and R1 is a coefficient defined below on the basis of TMP:

R1=1.0−(TMP/upper limit of TMP)·(1.0−r)

where r is a coefficient of the upper limit of pressure difference and set at an appropriate value between 0.0 (inclusive) and 1.00 depending on the degree of internal plugging of the separation membrane. Depending on the properties of the blood to be processed and the quality of the separation membrane, the separation membrane occasionally has a great tendency to be plugged. If it is empirically known that the separation membrane is likely to be plugged, the value of r is set in the lower range. On the other hand, if it is empirically known that the separation membrane is free from the potential plugging, the value of r may be set in the higher range.

The coefficient of plasma flow ratio K is a parameter which is set by the plasma flow ratio setting device in consideration of the performance of the plasma separator 4 and the properties of the blood to be processed and it is generally set within the range of 0.2 to 0.4, typically within the range of 0.25 to 0.35.

The operation of the plasma pump 5 is controlled on the basis of the monitored values of TMP which represents the pressure difference across the separation membrane in the plasma separator 4 and $\Delta$P4/6 (=P4−P6) representing the pressure difference across the adsorber 6. If TMP or $\Delta$P4/6 (=P4−P6) deviates from the respective limiting value, the plasma pump flow rate QP is rapidly reduced at the specified deceleration $Vp_2$ (e.g., 140 mL/min/min). If the pressure constraint is eventually removed, QP is increased again at the normal acceleration $Vp_1$ so that it is reverted toward the target plasma flow rate QPs.

It should be noted that the limiting values of the various pressures to be monitored, namely, the lower limit of blood collection pressure P1, the upper limit of venous blood pressure P7, the upper limit of the pressure difference across the plasma separator $\Delta$P2/6, the upper limit of the pressure difference across the separation membrane TMP and the upper limit of the pressure difference across the adsorber $\Delta$P4/6, are each set to be a little lower than the threshold for the issuance of an alarm signal so as to assure safety in the treating operations. Specifically, a difference of about 20 mmHg is provided between the threshold and the respective limiting value.

The plasma pump 5 is not operated independently of the blood pump 2 but the two pumps are controlled in operative association with each other. Even if the plasma pump 5 is running normally, it may become necessary to reduce the blood pump flow rate QB on account of a pressure constraint; in that case, the plasma pump flow rate QP is reduced synchronously such that the relation QP=K·R1·QB (for the definitions of K and R1, see above) is maintained at all times. If the blood pump flow rate QB is adjusted to be equal to the standby flow rate QBa when an abnormal event (as in valves) which is other than pressure constrains occurs, the plasma pump 5 is brought to a stop.

In the embodiment under consideration, the plasma pump 5 is so set that it will stop running if the blood pump flow rate QB falls below a certain value (e.g. 15 mL/min). It should, however, be noted that the lower limit of QB below which the plasma pump 5 is brought to a stop is not necessarily 15 mL/min but may be determined as appropriate for parameters such as the performance of the pumps.

After the pressure constraints and other abnormal events are removed, the plasma pump flow rate QP is restored from the rest state and the procedure for the restoration is essentially the same as the already-described procedure for starting the operation of the plasma pump 5.

The second embodiment of the invention is shown in FIG. 3 and relates to an apparatus for removing the unwanted cholesterol from plasma in two adsorbers. In this particular embodiment, two adsorbers 6A and 6B are provided in parallel in the plasma circuit 3 and flow channels are formed in such a way that the two adsorbers 6A and 6B can be operated alternately; in addition, while one adsorber is being used, the other is reactivated with a regenerating fluid, thereby enabling both adsorbers to be used repeatedly such that plasma is processed with the regeneratable adsorbers.

The apparatus of plasma treatment used in the second embodiment shares the blood collection circuit 1 and return circuit 7 with the apparatus of plasma treatment of the first embodiment. However, the plasma circuit differs in that two branches are formed downstream of the plasma pump 5 and respectively provided with two parallel adsorbers 6A and 6B of the same capacity; in addition, a replacement fluid pump 12 is provided upstream of the adsorbers 6A and 6B and connected to means for supplying an regenerating fluid 13 (a concentrated aqueous solution of an electrolyte such as sodium chloride) and means for supplying a replacement fluid 14 (e.g. physiological saline or Ringer's solution). Fluid shortage detectors 23, 24, and 25 are also provided. Switching between the parallel adsorbers 6A and 6B, as well as the feeding of each adsorber with a suitable fluid selected among plasma, regenerating fluid and replacement fluid can be accomplished by opening or closing valves V1 to V11. Another feature to be added in the second embodiment is a drip chamber D5 fitted with a pressure gauge P5 for detecting the pressure between the replacement fluid pump 12 and either adsorber 6A and 6B.

Using the thus constructed apparatus of plasma treatment of a regeneratable type, plasma will be treated in accordance with the following procedure. After the specified preparatory steps such as setting up the respective circuits and rinsing their interior have ended, a blood sample is withdrawn into the collection circuit 1 by means of the blood pump 2 and plasma is separated from the blood in the plasma separator 4. The separated plasma is directed into one of the two adsorbers 6A and 6B by means of the plasma pump 5. The method of controlling the pumps in such plasma treating steps is substantially the same as in the first embodiment. Stated specifically, after the blood pump 2 is turned on, the blood pump flow rate is first increased at the initial acceleration $Vb_0$ which is set at an appropriate value in the range of 20 to 100 mL/min/min; when the integrated blood flow has reached 300 mL, the initial acceleration $Vb_0$ is switched to the normal acceleration $Vb_1$ which is set at an appropriate value in the range of 20 to 150 mL/min/min and the blood pump flow rate is increased until the target value QBs (=100 mL/min) is reached. When QBs has been reached, the blood pump 2 is controlled such as to maintain this value based on the monitored values of P1, P2 and ΔP2/6.

Referring now to the plasma pump 5, it remains at rest until after the blood pump has run until the blood pump flow rate QB reaches 15 mL/min. When QB has reached 15 mL/min, the plasma pump 5 is started. In this case, the associated valves are manipulated to form a flow channel that permits the plasma to flow only into the adsorber 6A. The plasma pump flow rate QP is increased at the initial acceleration $Vp_0$ (10–60 mL/min/min) until the integrated plasma flow reaches 50 mL. After the integrated plasma flow has reached 50 mL, QP is increased at the normal acceleration $Vp_1$ which is set at an appropriate value in the range of 10 to 100 mL/min/min until the target plasma flow rate QPs is reached. The target value QPs is the product of multiplication of QBs (=the target blood flow rate for the blood pump) by K (=the coefficient of plasma flow ratio which is preset by the plasma flow ratio setting device) and R1 which is determined from TMP (=the pressure difference across the separation membrane in the plasma separator 4). When QPs has been reached, the plasma pump 5 is controlled at every moment such as to maintain this value based on the monitored values of TMP and ΔP4/6.

If the blood pump 2 undergoes a pressure constraint in association with either one of P1, P7 and ΔP2/6, the blood pump flow rate QB is reduced rapidly at the deceleration $Vb_2$ (=300 mL/min/min) to ensure that the pressure constraint is removed as soon as possible. When the pressure constraint is removed, the blood pump flow rate QB is increased at the normal acceleration $Vb_1$ such that it is reverted toward the target blood flow rate QBs (=100 mL/min).

As in the case of the blood pump 2, if the plasma pump 5 undergoes a pressure constraint in association with TMP or ΔP4/6, the plasma pump flow rate QP is reduced rapidly at the specified deceleration $Vp_2$ (e.g. 140 mL/min/min). If the pressure constraint is removed, the plasma pump flow rate QP is increased again at the normal acceleration $Vp_1$ such that it is reverted toward the target plasma flow rate QBs.

If an abnormal event (as in valves) which is other than the pressure constraints occurs, the blood pump 2 is decelerated rapidly only when it is running without any troubles and blood circulation is effected by controlling the blood pump 2 to provide the standby flow rate QBa which is set by the blood flow rate setting device so as not to exceed 50 mL/min. In this case, the plasma pump 5 should in principle be brought to a stop. When the abnormal event under consideration is removed, the blood pump flow rate QB is reverted toward the target value QBs.

If a pressure constraint develops to cause the necessity of reducing the blood pump flow rate QB, the plasma pump flow rate QP is reduced synchronously. In this case, too, the plasma pump flow rate QP is controlled to maintain the relation QP=K·R1·QB. In addition, the plasma pump 5 is so set that if the blood pump flow rate QB has fallen below 15 mL/min, it stops running.

Figure 4:
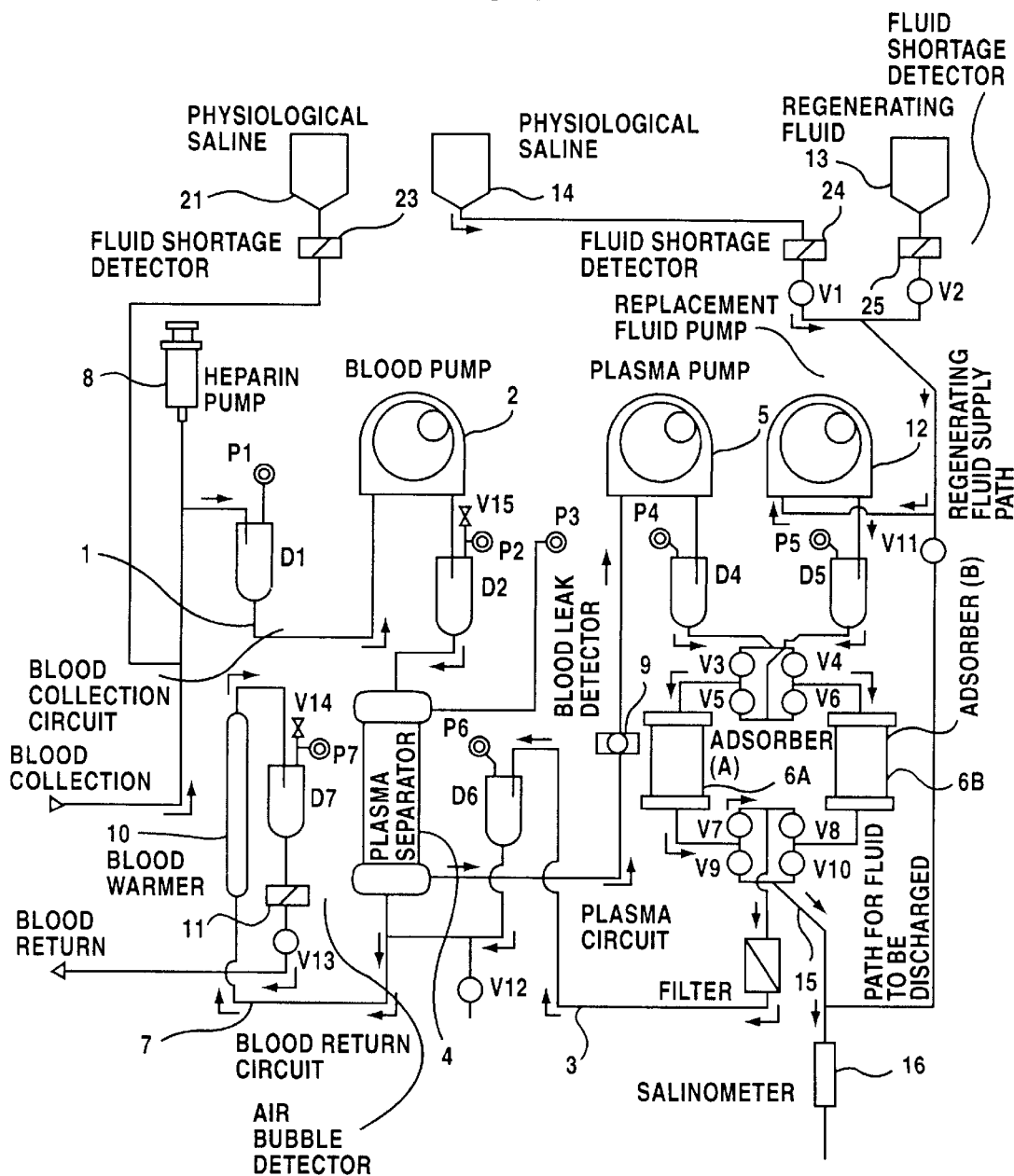
FIG. 4 is a diagram showing schematically the flow channels formed after switching between the two adsorbers in the apparatus of plasma treatment according to the second embodiment of the invention.

If, as the result of execution of plasma treatment, the treating capacity of adsorber 6A has dropped below a certain level or if the integrated throughput has reached a specified value, the present set of flow channels is switched to another set of flow channels by manipulation of the associated clamp valves; in the new set of flow channels, the replacement fluid (e.g., physiological saline) is flowed into the adsorber 6A by means of the replacement fluid pump 12 and the plasma is flowed into the adsorber 6B, with the outlet portion of the adsorber 6A being connected to the return circuit 7 whereas the outlet portion of the adsorber 6B is connected to a reject flow channel 15. The configuration of the flow channels just described above is shown in FIG. 4.

Subsequently, the adsorber 6A is supplied with the replacement fluid by means of the replacement fluid pump 12 and the plasma is forced out of the adsorber 6A to be returned to the patient through the return circuit 7. On the other hand, the adsorber 6B is supplied with an incoming flow of plasma, which displaces the internal preservative fluid such that the latter is discharged through the reject flow channel 15. When the plasma has been forced out of the adsorber 6A such that its interior is filled up by the replacement fluid, the outlet portion of the adsorber 6A is disconnected from the return circuit 7 and connected to the reject flow channel 15. Similarly, when the interior of the adsorber 6B has become devoid of the permeate to be filled up with the plasma, the outlet portion of the adsorber 6B is disconnected from the reject flow channel 15 and connected to the return circuit 7 so that the plasma treatment is continued by operation of the adsorber 6B.

Figure 5:
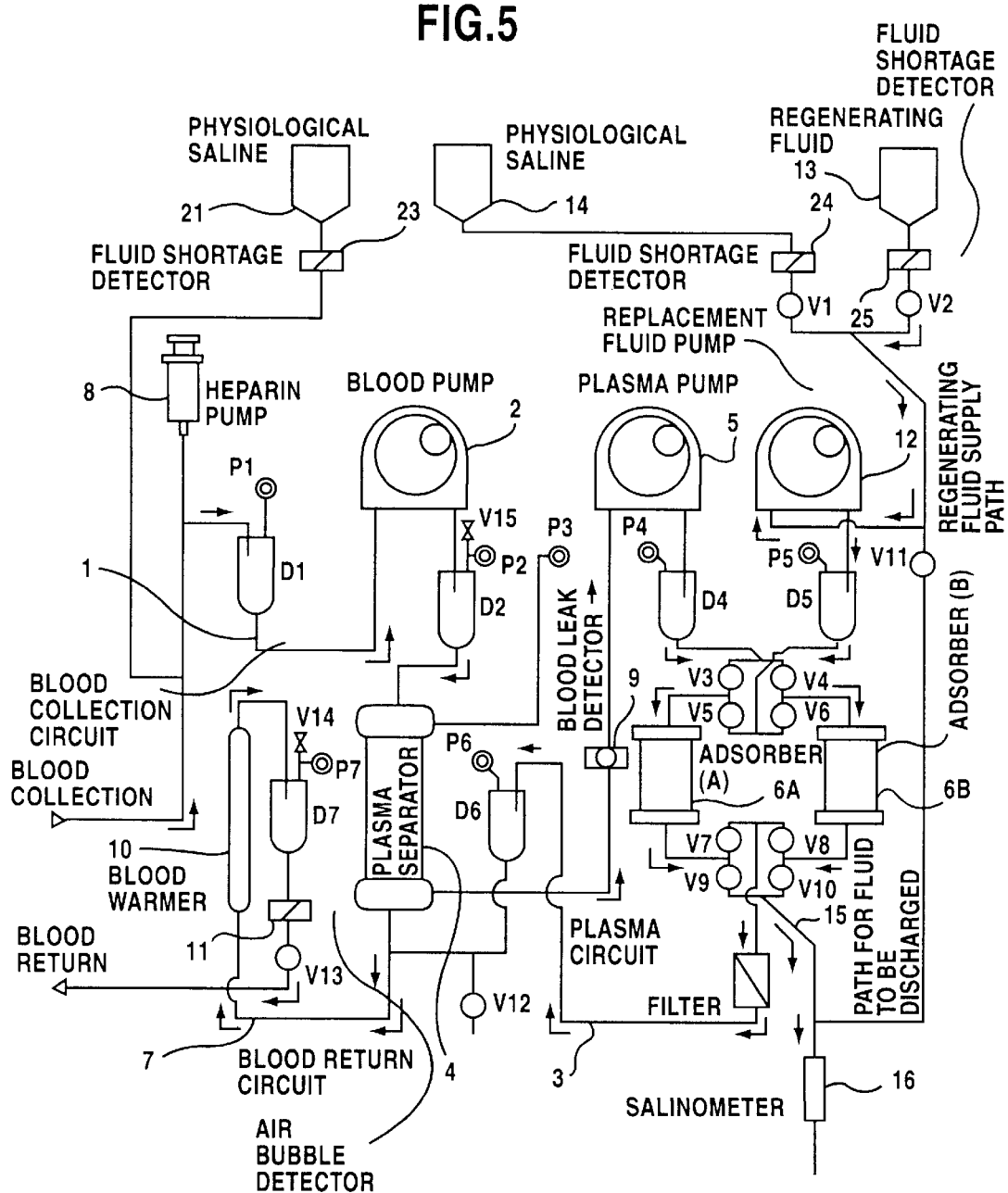
FIG. 5 is a diagram showing schematically the flow channels used to regenerate one of the two adsorbers in the plasma processor according to the second embodiment of the invention.

While the plasma is being treated with the adsorber 6B, a flow channel is formed to establish communication between the inlet portion of the adsorber 6A and the regenerating fluid supply means 13 such that the regenerating fluid is fed into the adsorber 6A by means of the replacement fluid pump 12. The regenerating fluid regenerates the adsorbent in the adsorber 6A so that its adsorptive power is restored. The configuration of flow channels formed in this case is shown in FIG. 5.

When the passage of the regenerating fluid has reached a specified value, the inlet portion of the adsorber 6A is allowed to communicate again with the replacement fluid supply means 14 and the replacement fluid is supplied so that the regenerating fluid is discharged from within the adsorber 6A. Since the regenerating fluid has a higher salt concentration than the physiological level, it needs to be replaced by the replacement fluid to ensure that the interior of the adsorber 6A is restored to the physiological concentration.

The reject flow channel 15 is provided with a salinometer 16 by means of which one can confirm that the regenerating fluid has been completely replaced by the replacement fluid to provide a reject in which the salt concentration has been reverted to the physiological level.

Thus, the adsorptive capacity of the adsorber 6A has been restored and its interior has been filled up with the replacement fluid. When the adsorptive capacity of the other adsorber 6B has thereafter fallen below a certain level or if the integral throughout has reached a specified value, the same procedure as described above may be employed to switch from adsorber 6B to 6A for performing plasma treatment. The adsorber 6B is then subjected to the same regeneration process as applied to the adsorber 6A, thereby recovering the adsorptive capacity of 6B. In this way, the two adsorbers 6A and 6B can be used alternately after the necessary regeneration process is performed and, hence, a large volume of plasma can be treated continuously even if these adsorbers have a comparatively small capacity.

The replacement fluid pump 12 is operated by a method which is substantially the same as the method of operating the plasma pump 5. Specifically, immediately after the start of its operation, the replacement fluid pump flow rate QR is increased at an initial acceleration $Vr_0$ which is set within the range of 10 to 60 mL/min/min. When the integrated flow has reached 50 mL, QR is increased at a normal acceleration $Vr_1$ which is set at an appropriate value within the range of 10 to 100 mL/min/min until the target replacement fluid flow rate QRs is reached. The target replacement fluid flow rate QRs is the product of multiplication of QBs (=the target blood flow rate for the blood pump) and the coefficient R1 which is determined from TMP (=the pressure difference across the separation membrane in the plasma separator 4). In other words, QRs representing the target replacement fluid flow rate for the replacement fluid pump 12 is set to be substantially equal to QPs which represents the target plasma flow rate for the plasma pump. If this condition is met, switching between the two adsorbers can be accomplished without compromising the purpose of realizing smooth continuation of the plasma treatment because the speed at which the replacement fluid forces the plasma out of the adsorber 6A is equal to the speed at which plasma flows into the other adsorber 6B.

After the target replacement fluid flow rate QRs has been reached, the replacement fluid pump 12 is controlled so as to maintain that value based on the monitored value of ΔP5/6 (=P5−P6) which represents the pressure difference across each adsorber 6A and 6B.

If the pressure being monitored deviates from the limiting value to cause a pressure constraint, the replacement fluid pump flow rate QR is rapidly reduced at a specified deceleration $Vr_2$ (e.g. 140 mL/min/min) If the pressure constraint is eventually removed, QR is increased again at the normal acceleration $Vr_1$ so that it is reverted toward the target replacement fluid flow rate QRs.

Even if the replacement fluid pump 12 is running normally, it may become necessary to reduce the blood pump flow rate QB on account of a certain abnormality such as a pressure constraint; in that case, the replacement fluid pump flow rate QR is reduced synchronously at the deceleration which is controlled to be equal to QB multiplied by K and R1 (for their definitions, see above). In the second embodiment of the invention, the replacement fluid pump 12 is so set that it will stop running if the blood pump flow rate QB falls below 15 mL/min. If the pressure constraint and other abnormal events have been removed, the replacement fluid pump 12 flow rate QR is restored by a procedure which is substantially the same as described above.

According to the forgoing embodiments of the present invention, plasma is treated in such a way that when the pressures being monitored by specified pressure gauges deviate from the respective limiting values to cause pressure constraints, various pump flow rates are reduced rapidly enough to ensure that the pressure constraints can be removed as soon as possible. After the pressure constraints are removed, the pump flow rates are restored at preset accelerations, again ensuring that there will be no excessive pressure buildups due to abruptly increasing loads.

If the blood pump flow rate is increased through two stages of acceleration when a blood sample is introduced immediately after the apparatus is started to operate, there will be no possibility of imposing an abrupt load on the apparatus and the target blood flow rate can be rapidly reached without causing a pressure buildup exceeding the limiting value. This is also true with the plasma pump 5 and if its flow rate is increased through two stages of acceleration, the desired target plasma flow rate can be rapidly reached without causing a departure from the limiting value of pressure.

If any abnormal event other than pressure constraints occurs while the blood pump 2 is operating normally, blood pump 2 is controlled in such a way that its flow rate is decelerated rapidly while a standby flow rate is maintained at a value not exceeding a preset upper limit; this ensures safety in the blood treatment without stopping its flow, thereby preventing the blood from being coagulated in the circuits.

If the plasma pump flow rate is controlled as a function of the pressure difference across the separation membrane in the plasma separator 4, it can be set at an optimal value reflecting the degree of plugging of the separation membrane which is variable at every moment. As a result, the progress of the plugging of the separation membrane can be retarded and the required plasma treatment can be accomplished without being interrupted or undergoing some constraints.

Figure 6:
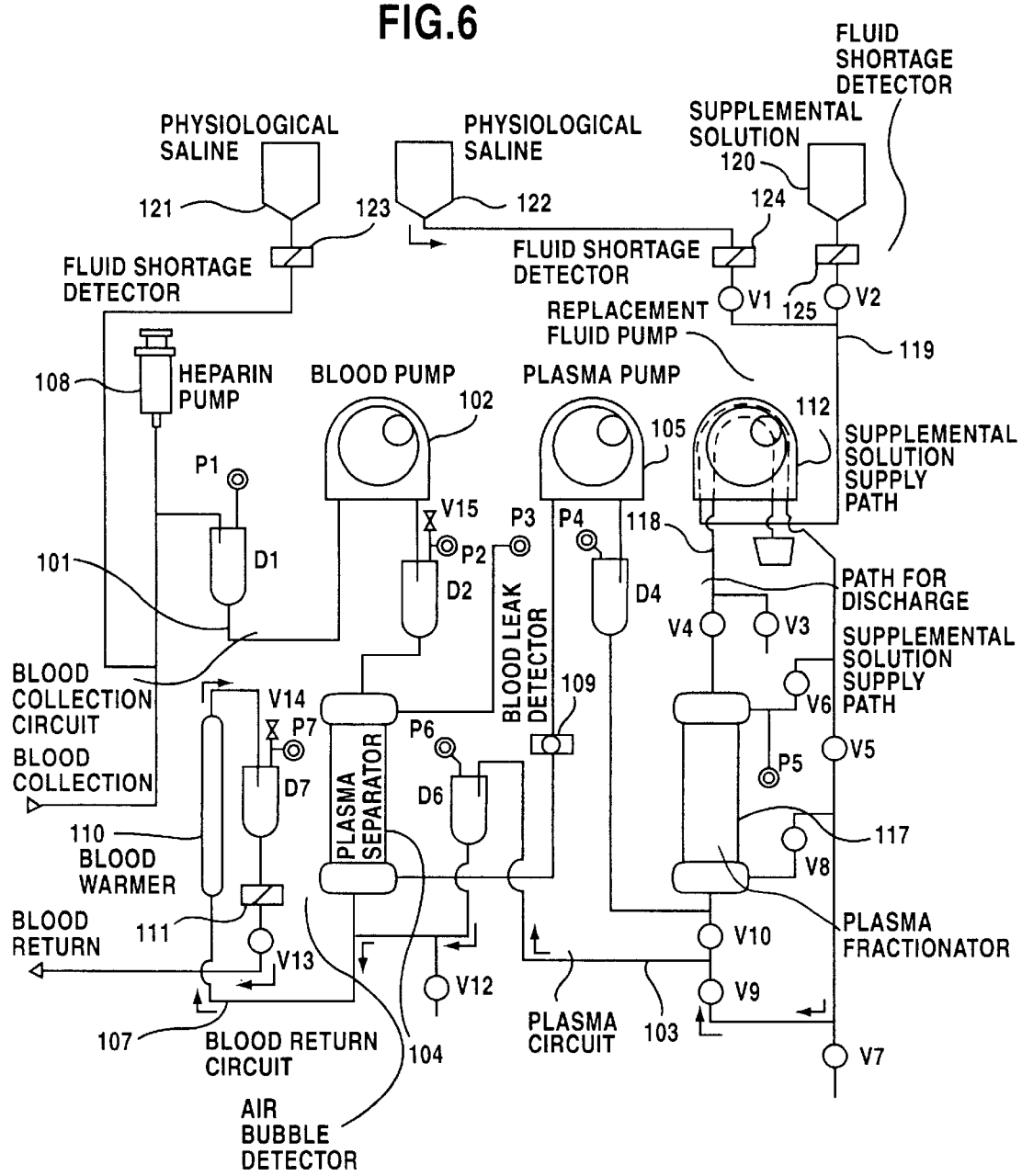
FIG. 6 is a diagram showing schematically the configuration of circuits in the apparatus of plasma treatment of the invention.

FIG. 6 shows an apparatus for treating plasma by double filtration and comprises basically a collection circuit 101 for withdrawing a blood sample and feeding it into a plasma separator 104 by means of a blood pump 102, a plasma circuit 103 in which the plasma separated in the plasma separator 104 is directed by means of a plasma pump 105 into a plasma fractionator 117, where it is fractionated into a high-molecular weight component and a low-molecular weight component, the latter being returned to the patient, an ejection channel 118 through which the high-molecular weight component of the plasma is discharged by means of a replacement fluid pump 112, a replenishing fluid supply channel 119 which communicates replenishing solution supply means 120 with the plasma circuit 103 via the replacement fluid pump 112, and a return circuit 107 in which the low-molecular weight component of the plasma as supplied with the replenishing fluid is combined with the blood permeate from the plasma separator 104 and the replenishing fluid and returned to the patient.

In the embodiment to be described below, a replacement fluid pump 112 of a twin type is employed. This provides for simultaneous fitting of two tubes, one serving as a channel for discharging the high-molecular weight component of plasma and the other serving as a flow channel for feeding the replenishing fluid. As a result, the discharge of the high-molecular weight component of plasma through the first tube and the passage of the replenishing fluid through the second tube can be accomplished simultaneously with a single pump unit, thereby assuring the high-molecular weight component of plasma to be exchanged with an equal volume of the replenishing fluid.

Provided at appropriate sites in the circuits are pressure gauges P3 and P5, drip chambers D1, D2, D4, D6 and D7 fitted with pressure gauges P1, P2, P4, P6 and P7, as well as valves V1 to V10 and V12 to V15 for performing ON/OFF and switching control over the flow channels. Also provided are infusers of physiological saline 121, 122 for rinsing the circuits and recovering the residual blood, an infuser of anticoagulant heparin 108, a blood leak detector 109 for detecting the leakage of blood into the plasma emerging from the plasma separator 104, a blood warmer 110 for warming the returning blood to a specified temperature, an air bubble detector 111 for detecting the entrance of air bubbles into the returning blood, fluid shortage detectors 123, 124 and 125 for checking the supply of physiological saline and replenishing fluid, and any other necessary devices.

The procedure of plasma treatment by double filtration will now be outlined. Usually, the execution of plasma treatment is preceded by the preparative steps of setting up the respective circuits and rinsing their interior with physiological saline. When the required preparative steps end, the blood pump 102 is started to run so that a blood sample is withdrawn into the collection circuit 101 through the collection tip and thence supplied into the plasma separator 104. The plasma separated from the blood in the plasma separator 104 is forced by means of the plasma pump 105 to be directed into the plasma fractionator 117, where it is fractionated into the high-molecular weight component and the low-molecular weight component. The high-molecular weight component of plasma contains deleterious or unwanted matter and, hence, is discharged through the ejection channel 118 by means of the replacement fluid pump 112. As already mentioned, the replacement fluid pump 112 is of a twin type which is fitted with both the tube serving as a channel for discharging the high-molecular weight component of plasma and the tube serving as a channel for feeding the replenishing fluid; hence, as the high-molecular weight component of plasma is discharged, the same volume of the replenishing fluid is supplied from its supply means 113 into the low-molecular weight component of plasma through the associated feed channel. The thus replenished low-molecular weight component of plasma is combined with the blood permeate from the plasma separator 104 and returned to the patient through the blood warmer 110. When a specified amount of plasma has been treated, physiological saline is introduced into the circuits such that the residual plasma and blood are recovered from the circuits and returned to the patient.

The replacement fluid pump 112 is adapted to be such that if the monitored value of TMP2 (=P4−P5) which represents the pressure difference across the separation membrane in the plasma fractionator is less than a preset threshold pressure Pα (TMP2<Pα), it will not start to run whereas if TMP2 is equal to or greater than Pα(TMP2≧Pα), it will start to run. This is because if the replacement fluid pump 112 is actuated before TMP2 has risen sufficiently to reach Pα, the low-molecular weight component of plasma can potentially be lost into the high-molecular weight component being discharged.

On the other hand, if TMP2 is equal to or greater than Pα, it can safely be concluded that the high-molecular weight component of plasma is being effectively separated from the low-molecular weight component in the plasma fractionator 117. Therefore, if the replacement fluid pump 112 is adapted to run only if TMP2≧Pα, there is no possibility for the low-molecular weight component of plasma to be lost into the high-molecular weight being discharged. In addition, if TMP2 becomes less than the pressure setting Pα during the operation of the replacement fluid pump 112 because of abnormality in a certain device such as the plasma fractionator 117, the plasma circuit 103 or valves, the replacement fluid pump 112 is immediately brought to a stop so as to prevent the loss of plasma.

After the start of operation of the replacement fluid pump 112, its flow rate QR is increased at a specified acceleration $Vr_1$ toward the target replacement fluid flow rate QRs which is preset by a replacement fluid flow rate setting device. It should, however, be noted that QR satisfies the condition that it be by no means greater than a prescribed flow rate QRa=cQP (0<c<1). In other words, QR or the replacement fluid pump flow rate is controlled to be such that it is always equal to whichever smaller of the target replacement fluid flow rate QRs or the prescribed flow rate QRa. By this control, the rate of discharging the high-molecular weight component of plasma is effectively restricted to prevent the loss of the low-molecular weight component of plasma into the high-molecular weight.

While the replacement fluid pump 112 is operated to provide the target replacement fluid flow rate QRs, abnormal events such as pressure constraints may give rise to the need for reducing the plasma pump flow rate QP, with the result that the prescribed flow rate QRa which depends on QP becomes lower than the target replacement fluid flow rate QRs. In this case, the replacement fluid pump flow rate QR is reduced to the prescribed flow rate QRa.

When the abnormal events such as pressure constraints are removed and the plasma pump flow rate QP is restored, eventually causing the prescribed flow rate QRa to exceed the target replacement fluid flow rate QRs, the replacement fluid pump flow rate is increased again toward QRs at an acceleration which is set at $Vr_1$.

Generally speaking, if the settings of pump flow rates are very small, the operation of the pumps becomes unstable, causing frequent fluctuations in their flow rates. Therefore, if the target replacement fluid flow rate QRs for the replacement fluid pump 112 is set below a certain value or if the prescribed flow rate QRa becomes lower than a certain value due to the drop in the plasma pump flow rate, the replacement fluid pump 112 is controlled to perform an intermittent operation, in which it runs and stops alternately. By executing such intermittent operation, one can assure the precision in the rotation of the replacement fluid pump 112 in an extremely small flow rate range, thereby permitting the replacement fluid flow rate to be stabilized. In addition, the intermittent operation of the replacement fluid pump 112 is equivalent to opening and closing the ejection channel 118 continually, thereby making it possible to ensure that TMP2 which represents the pressure difference across the separation membrane in the plasma fractionator 117 is maintained at a high level. As a result, the efficiency of separation of the low-molecular weight component of plasma from the high-molecular weight component is sufficiently improved to prevent the loss of plasma. The value of QRs or QRa at which the replacement fluid pump 112 is allowed to operate intermittently is determined as appropriate for the performance of the pump.

Figure 7A:
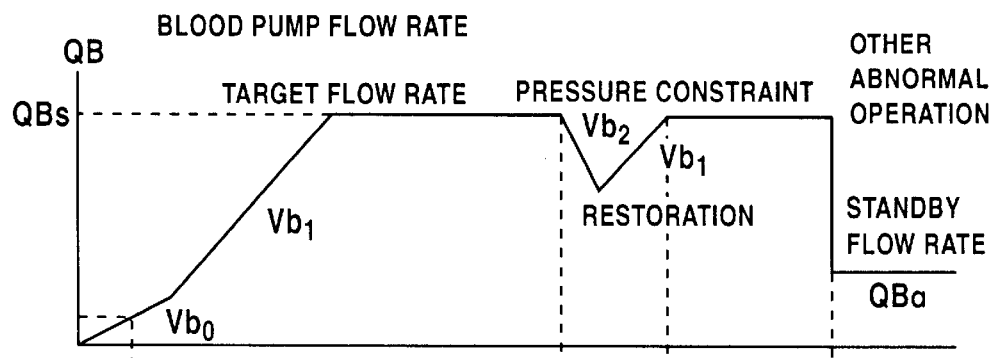
FIGS. 7A, 7B and 7C are graphs showing how various pumps are controlled in the plasma treating method of the invention.
Figure 7B:
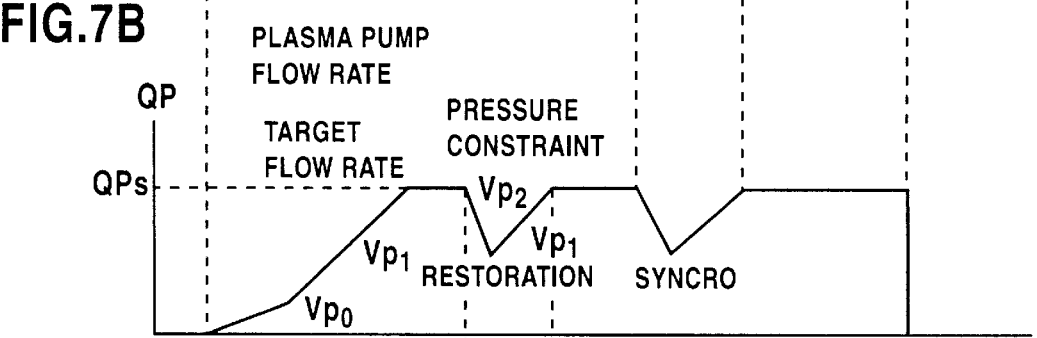
Figure 7C:
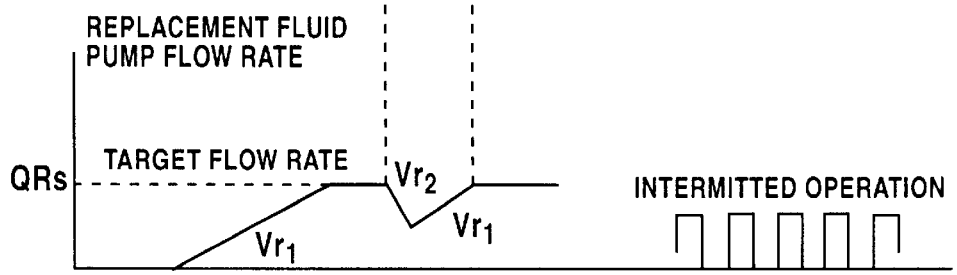

The above-described procedures for the control of the blood pump 102, plasma pump and the replacement fluid pump 112 may be represented graphically in FIGS. 7A, 7B and 7C. (Plasma treating steps)

An example of the method of setting conditions for the case of executing the plasma treating steps by means of the apparatus of plasma treatment shown in FIG. 6 will now be described below.

Immediately after the start of operation of the blood pump 102, its flow rate QB is increased at the initial acceleration $Vb_0$ which is set at an appropriate value within the range of 20 to 100 mL/min/min. When the integrated blood flow has reached 300 mL which is approximately equal to the sum of the capacities of the collection circuit 101 and the plasma separator 104, the initial acceleration $Vb_0$ is switched to the normal acceleration $Vb_1$ which is set at an appropriate value within the range of 20 to 150 mL/min/min and the blood pump flow rate is increased until the target flow rate QBs (=100 mL/min) is reached. The initial acceleration $Vb_0$ is typically set to be smaller than the normal acceleration $Vb_1$ but this is not always the case of the invention. When the blood flow rate has reached the target blood flow rate QBs, the operation of the blood pump 102 is controlled so as to maintain QBs.

The operation of the blood pump 102 is controlled in such a way that the monitored values of the blood collection pressure P1, the venous blood pressure P7 and the pressure difference across the plasma separator ΔP2/P6 will not exceed the limits of the respective values. If either one of said pressures deviates from the associated limiting value to cause a pressure constraint, namely, if P1 becomes lower than the lower limit, or if P7 exceeds the upper limit, or if ΔP2/6 becomes greater then the upper limit, the blood pump flow rate QB is rapidly reduced at a sufficiently great deceleration of $Vb_2$ (=300 mL/min/min) to ensure that the pressure constraint is removed as soon as possible. When the pressure constraint is removed, the blood pump flow rate QB is increased again at the normal acceleration Vb until the target blood flow rate QBs (=100 mL/min) is restored.

If there occurs an abnormal event other than the pressure constraints, as exemplified by abnormal operation of valves, and yet the blood pump 102 is running without trouble, the blood pump flow rate QB is rapidly decelerated to the standby flow rate QBa (≦50 mL/min) which is preset by the blood flow rate setting device and the blood circulation is continued by controlling the blood pump 102 such as to maintain QBa. If the abnormal event under consideration is removed, QB is restored to the target blood flow rate QBs. The procedure of executing the restoration to QBs has already been described above.

Referring now to the plasma pump 105, it remains at rest until after the blood pump 102 has run to attain a QB value of 15 mL/min. When QB has reached 15 mL/min, the plasma pump 105 is started to run. Until after the integrated plasma flow has reached 50 mL which is approximately equal to the volume of plasma on the secondary side of the plasma separator 104, the plasma pump flow rate QP is increased at the initial acceleration $Vp_0$ which is set within the range of 10 to 60 mL/min/min. Once the integrated plasma flow has reached 50 mL, the plasma pump flow rate QP is increased at the normal acceleration $Vp_1$ (10 to 100 mL/min/min) until it reaches the target plasma flow rate QPs. In order to ensure that the load on the machine parts will increase mildly, the normal acceleration $Vp_1$ is usually set to be greater than the initial acceleration $Vp_0$.

The plasma pump flow rate QP is controlled at every moment such as to maintain the target plasma flow rate QPs which is calculated on the basis of the blood pump flow rate QB and the pressure difference across the separation membrane in the plasma separator 104 which is denoted by TMP1 [=(P2+P6)/2−P3].

The target plasma flow rate QPs is expressed as QPs= K·R1·QB, where QB is the blood pump flow rate, K is a coefficient of plasma flow ratio which is preset by a plasma flow ratio setting device and R1 is a coefficient defined below on the basis of TMP1:

R1=1.0−(TMP1/upper limit of TMP1)·(1.0−r)

where r is a coefficient of the upper limit of pressure difference and set at an appropriate value between 0.0 (inclusive) and 1.00 depending upon the degree of internal plugging of the separation membrane. Depending upon the properties of the blood to be treated and the quality of the separation membrane, the separation membrane occasionally has a great tendency to be plugged. If it is empirically known that the separation membrane is likely to be plugged, the value of r is set in the lower range. On the other hand, if it is empirically known that the separation membrane is free from the potential plugging, the value of r may be set in the higher range.

The coefficient of plasma flow ratio K is a parameter which is set by the plasma flow ratio setting device in consideration of the performance of the plasma separator and the properties of the blood to be treated and it is generally set within the range of 0.2 to 0.4, typically within the range of 0.25 to 0.35.

If TMP1 deviates from the limiting value, the plasma pump flow rate QP is rapidly reduced at the specified deceleration $Vp_2$ (e.g., 140 mL/min/min) If the pressure constraint is eventually removed, QP is increased again at the normal acceleration $Vp_1$ so that it is reverted toward the target plasma flow rate QPs.

It should be noted that the limiting values of the various pressures to be monitored, namely, the lower limit of blood collection pressure P1, the upper limit of venous blood pressure P7, the upper limit of the pressure difference across the plasma separator ΔP2/6 and the upper limit of the pressure difference across the separation membrane TMP1, are each set to be a little smaller than the threshold for the issuance of an alarm signal so as to assure safety in the processing operations. Specifically, the difference of about 20 mmHg is provided between the threshold and the respective limiting value.

The plasma pump 105 is not operated independently of the blood pump 102 but the two pumps are controlled in operative association with each other. Even if the plasma pump 105 is running normally, it may become necessary to reduce the blood pump flow rate QB on account of a pressure constraint; in that case, the plasma pump flow rate QP is reduced synchronously such that the relation QP=K·R1·QB (for the definitions of K and R1, see above) is maintained at all times. If the blood pump flow rate QB is adjusted to be equal to the standby flow rate QBa when an abnormal event (as in valves) which is other than pressure constraints occurs, the plasma pump 105 should in principle be brought to a stop.

In the embodiment under consideration, the plasma pump 105 is so set that it will stop running if the blood pump flow rate QB falls below a certain value (e.g. 15 mL/min). It should, however, be noted that the lower limit of QB below which the plasma pump 105 is brought to a stop is not necessarily 15 mL/min but may be determined as appropriate for parameters such as the performance of the pumps.

After the pressure constraints and other abnormal events are removed, the plasma pump flow rate QP is restored from the rest state and the procedure for the restoration is essentially the same as the already-described procedure for starting the operation of the plasma pump 105.

The start of the replacement fluid pump is in principle regulated by TMP2 (=P4−P5) which represents the pressure difference across the separation membrane in the plasma fractionator 117, and the replacement fluid pump flow QR is not only controlled by the replacement fluid flow setting device but also restricted by the plasma pump flow rate QP.

The replacement fluid pump 112 is so set that it will stop when TMP2 is below the threshold pressure setting Pα(TMP2<Pα) whereas it starts to run if TMP2 is equal to or greater than Pα(TMP2≧Pα). The value of Pα is set at the smallest pressure difference (e.g. 50 mmHg) that is believed to achieve the required separation between the high- and low-molecular weight components of plasma by the separation membrane.

If TMP2 exceeds a limiting value (e.g. 300 mmHg), the situation is regarded as reflecting the extensive plugging of the separation membrane, so that the step of plasma fractionation is stopped and the process goes to the step of backflushing the separation membrane, which is described below.

Thus, the replacement fluid pump 112 will execute the operation for discharging the high-molecular weight component of plasma and the supply of the replenishing fluid only when TMP2 is within the range of 50 to 300 mmHg.

In another embodiment of the invention, the replacement fluid pump 112 may be actuated without reference to the setting of Pα. In this case, the operation of the replacement fluid pump 112 is controlled on the basis of the plasma pump flow rate QP.

In the usual situation, the replacement fluid pump flow rate QR is controlled to be equal to the target replacement fluid flow rate QRs (2.0 to 40 mL/min) which is set by the replacement fluid flow setting device. Specifically, immediately after the start of its operation, the replacement fluid pump flow rate is increased toward QRs at the preset acceleration $Vr_1$.

It should, however, be noted that the replacement fluid pump flow rate QR is so set that it will not exceed the prescribed flow QRa which is calculated on the basis of the plasma pump flow rate QP to be equal to cQP (0<c<1 and, in the usual case, c is set to be about 0.5). In other words, QR≦cQP is the condition that must preferentially be satisfied by the replacement fluid pump 112. Therefore, if pressure constraints or any other abnormal events make it necessary to reduce the plasma pump flow rate QP, thereby creating the relation cQP≦QRs, the replacement fluid pump flow rate QR is reduced until it becomes equal to cQP.

When the abnormal event is removed and the plasma pump flow rate QP is restored, causing the prescribed flow QRa to exceed the target replacement fluid flow rate QRs, the replacement fluid pump flow rate QR is increased toward QRs at the acceleration $Vr_1$.

The replacement fluid pump flow rate QR may sometimes be set within an extremely small range (e.g. 2 to 10 mL/min) as in the case where the target replacement fluid flow rate QRs is set at a very small value by means of the replacement fluid flow rate setting device or in the case where the prescribed flow rate QRa becomes very small due to the decrease in the plasma pump flow rate. In these cases, the replacement fluid pump 112 is operated intermittently in order to assure the precision of pump operation, thereby stabilizing the replacement fluid flow rate. The flow rate during the intermittent operation of the replacement fluid pump 112 may be defined in terms of a mean flow per minute.

By the intermittent operation of the replacement fluid pump, not only is the replacement fluid flow stabilized, but also, the channel for discharging the high-molecular weight component of plasma is continually opened and closed; hence, TMP2 can be maintained at a comparatively high value even if only a small amount of plasma is supplied to the plasma fractionator 117. As a result, the low-molecular weight component of plasma can be separated from the high-molecular component efficiently to prevent the loss of plasma.

(Plasma Recovery Step)

After the required plasma treating steps end, the residual plasma in the plasma fractionator 117 must be recovered and returned to the patient. To meet this need, the apparatus of plasma treatment of the example under discussion is adapted to be such that the plasma fractionator 117 can be supplied with physiological saline by means of the replacement fluid pump 112 from the physiological saline supply means 122 connected to the replenishing fluid supply channel 119.

Figure 8:
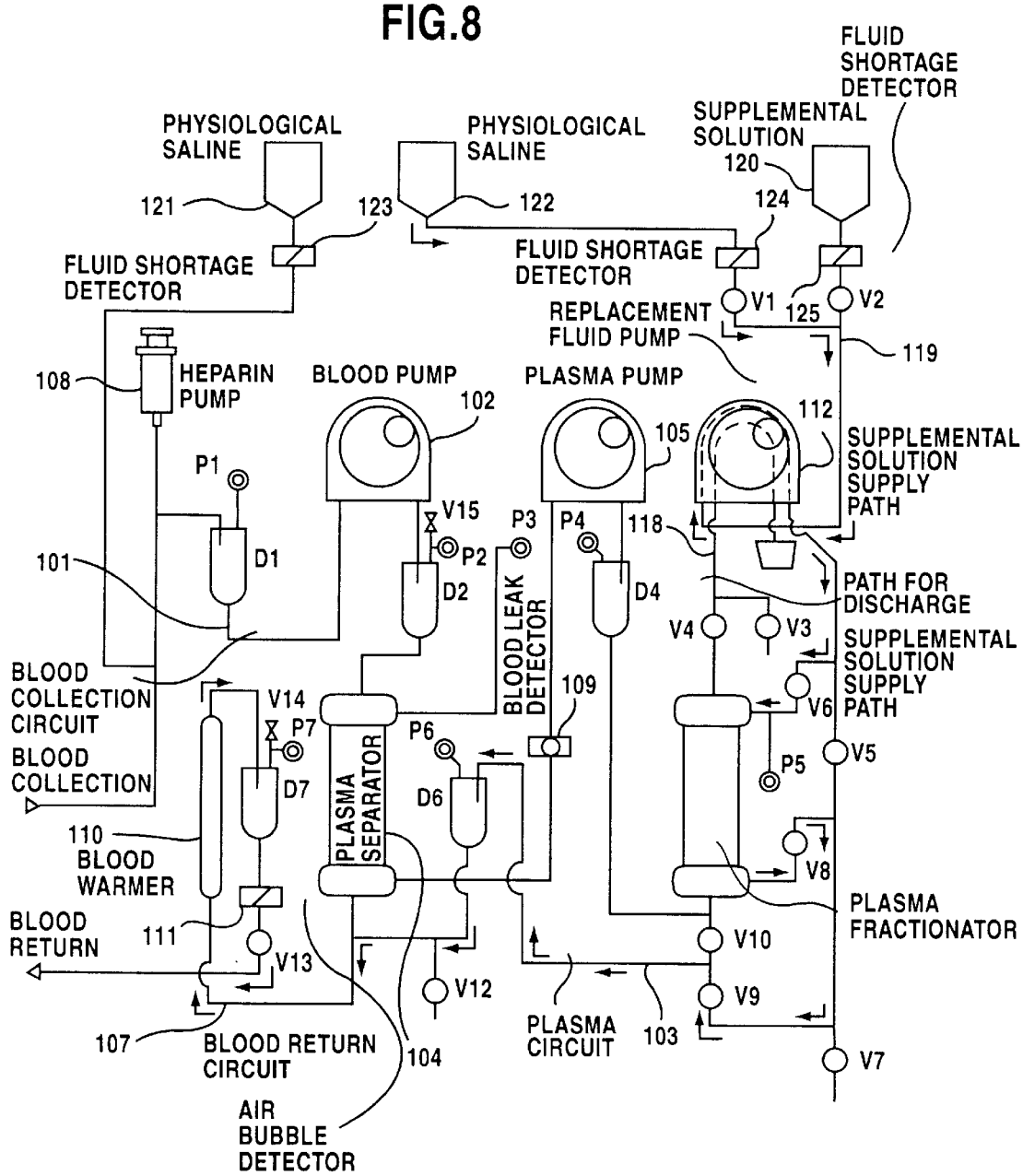
FIG. 8 is a diagram showing schematically the flow channel used to recover the residual plasma from the plasma fractionator in the apparatus of plasma treatment of the invention.

For plasma recovery, the associated valves are switched to form the necessary fluid channel as shown in FIG. 8 and physiological saline is introduced into the plasma fractionator 117 by means of the replacement fluid pump 112 so that the low-molecular weight component of plasma which remains outside the separation membrane in the plasma fractionator 117 is forced into the plasma circuit 103 and thence returned to the patient through the return circuit 107. In this case, the upper limit of QRs–1 which represents the target flow rate to be recovered through replacement by means of the replacement fluid pump 112 is 70 mL/min and, in addition, P5 representative of the pressure outside of the separation membrane is controlled not to exceed the upper limit of the venous blood pressure P7, which is set about 20 mmHg lower than the threshold for the issuance of an alarm signal.

(Backflushing Step)

During the plasma treatment, the separation membrane in the plasma fractionator 117 may be plugged to introduce difficulty in continuing the normal plasma treatment. This situation is recognized by the increase of TMP2 (typically above 300 mmHg) and can be dealt with by backflushing the separation membrane, in which physiological saline is supplied on the secondary side of the plasma fractionator 117 and allowed to flow from the outside to the inside of the separation membrane.

Figure 9:
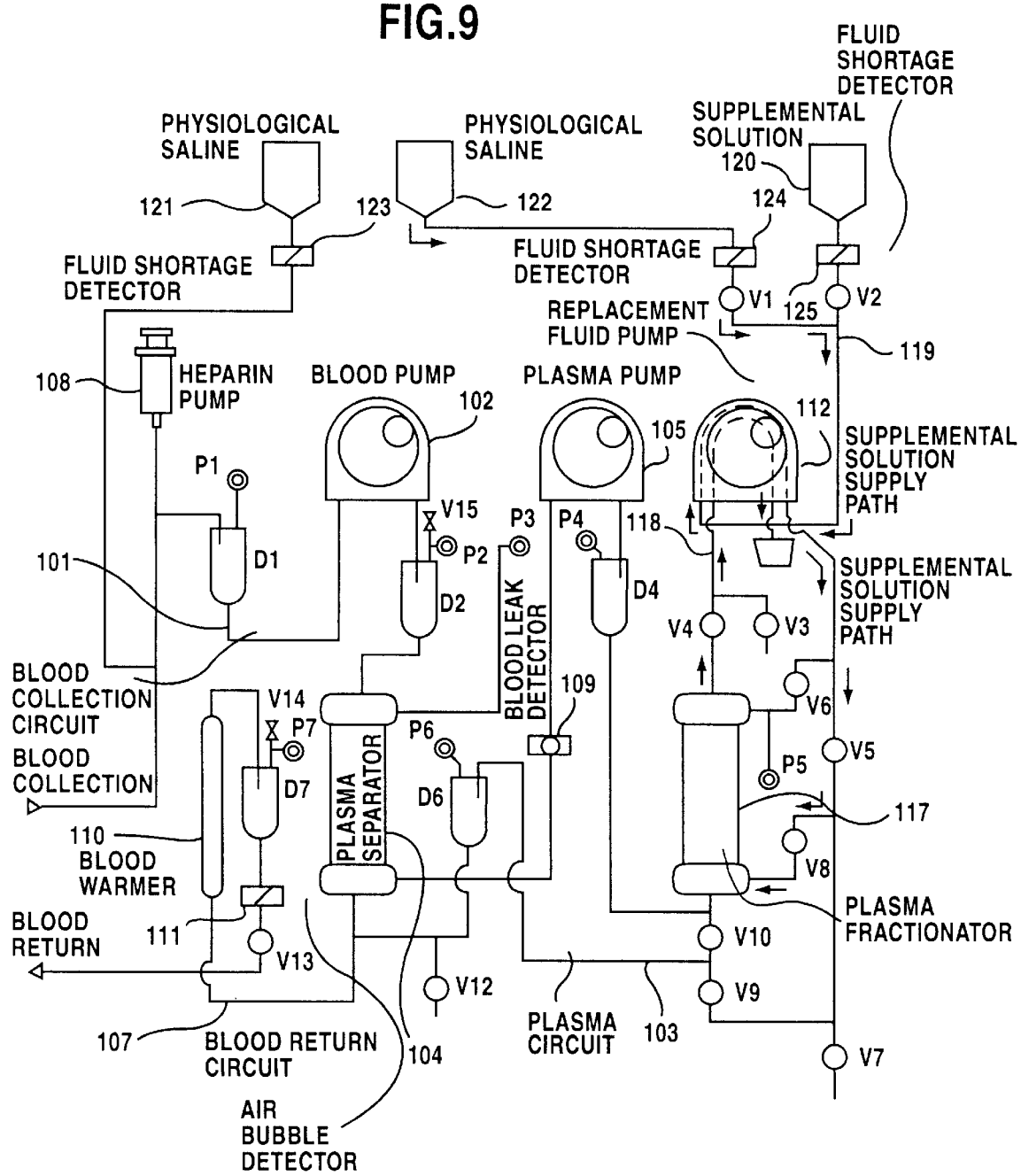
FIG. 9 is a diagram showing schematically the fluid channel used to backflush the separation membrane in the plasma fractionator in the apparatus of plasma treatment of the invention.

To perform the backflushing step, the necessary flow channel is formed as shown in FIG. 9 and the replacement fluid pump 112 is operated to supply physiological saline from its supply means 122 to the secondary side of the plasma fractionator 117 while discharging the fluid on the primary side of the separation membrane. In this case, the upper limit of QRs–2 which represents the target flow rate of backflushing through replacement by means of the replacement fluid pump 112 is 100 mL/min and, in addition, the pressure outside of the separation membrane being monitored by pressure sensor P5 is controlled not to exceed the upper limit, which is set about 20 mmHg lower than the threshold for the issuance of an alarm signal.

According to the embodiment of the present invention, plasma is processed in such a way that when the pressures being monitored by specified pressure gauges deviate from the respective limiting values to cause pressure constraints, various pump flow rates are reduced rapidly enough to ensure that the pressure constraints can be removed as soon as possible. After the pressure constraints are removed, the pump flow rates are restored at preset accelerations, again ensuring that there will be no excessive pressure buildups due to abruptly increasing loads.

If the blood pump flow rate is increased through two stages of acceleration when a blood sample is introduced immediately after the apparatus is started to operate, there will be no possibility of imposing an abrupt load on the apparatus and the target blood flow rate can be rapidly reached without causing a pressure buildup exceeding the limiting value. This is also true with the plasma pump 105 and if its flow rate is increased through two stages of acceleration, the desired target plasma flow rate can be rapidly reached without causing a departure from the limiting value of pressure.

If any abnormal event other than pressure constraints occurs while the blood pump 102 is operating normally, the blood pump 102 is controlled in such a way that its flow rate is decelerated rapidly while a standby flow rate is maintained at a value not exceeding a preset upper limit; this ensures safety in the blood treatment without stopping its flow, thereby preventing the blood from being coagulated in the circuits.

If the plasma pump flow rate is controlled as a function of the pressure difference across the separation membrane in the plasma separator 104, it can be set at an optimal value reflecting the degree of plugging of the separation membrane which is variable at every moment. As a result, the progress of the plugging of the separation membrane can be retarded and the required plasma treatment can be accomplished without being interrupted or undergoing some constraints.

If the condition for actuating the replacement fluid pump 112 is specified in terms of the pressure difference across the separation membrane in the plasma fractionator 117, with the upper limit of the replacement fluid pump flow rate being determined on the basis of the plasma pump flow rate, the high-molecular weight component of plasma can be discharged only when the low-molecular weight component is being separated efficiently; as a result, the loss of plasma can be prevented.

If the replacement fluid pump 112 is run intermittently, the precision of its operation in the range of extremely small flow rates is effectively maintained to permit for the stabilization of the flow rate. Hence, even if the replacement fluid pump 112 is operated at a very small flow rate, the pressure difference across the separation membrane in the plasma fractionator 117 can be maintained at a comparatively high level to ensure that the low-molecular weight component of plasma can be separated with high efficiency; as a result, the loss of plasma is prevented.

Figure 10:
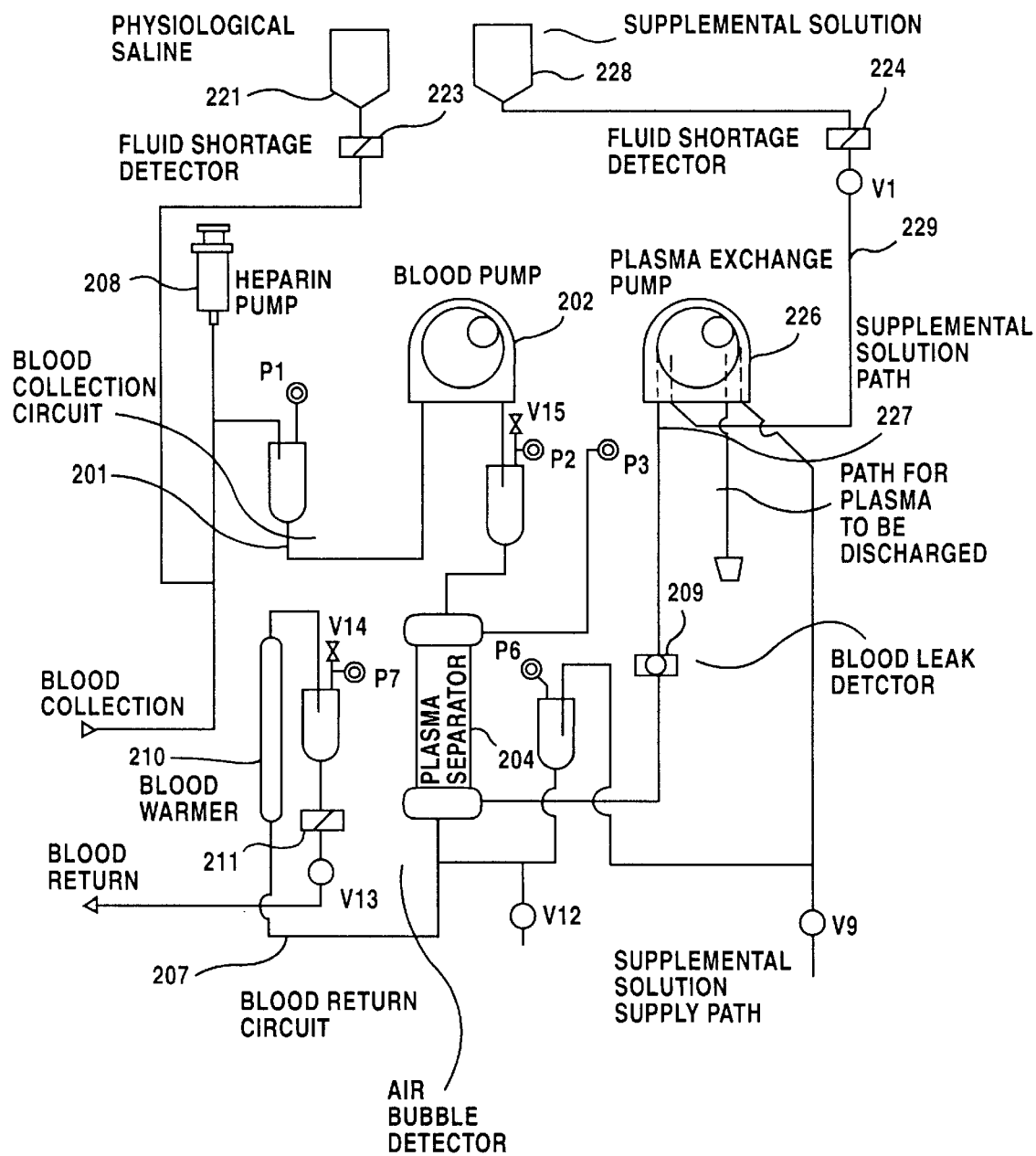
FIG. 10 is a diagram showing schematically the configuration of circuits in the apparatus of blood treatment of the invention.

FIG. 10 shows an apparatus for treating blood by plasma exchange and comprises basically a collection circuit 201 for withdrawing a blood sample and feeding it into a plasma separator 204 by means of a blood pump, 202 a plasma exchange pump 226, a reject plasma channel 227 for separating plasma from the blood in the plasma separator 204 and discharging the separated plasma by means of the plasma exchange pump 226, means of supplying a replenishing fluid 228, a replenishing fluid supply channel 229 for communicating the replenishing fluid supply means with a return circuit 207 via the plasma exchange pump 226, and the return circuit 207 for returning the blood permeate from the plasma separator 204 after it is combined with the replenishing fluid.

In the embodiment to be described below, a plasma exchange pump 226 of a twin type is employed. This provides for simultaneous fitting of two tubes, one serving as the reject plasma channel 227 and the other serving as the replenishing fluid supply channel 229. As a result, the passage of plasma through the reject plasma channel 227 and that of the replenishing fluid through the replenishing fluid supply channel 229 can be accomplished simultaneously with a single pump unit, thereby assuring the plasma to be exchanged with an equal volume of the replenishing fluid.

Provided at appropriate sites in the circuits are a pressure gauge P3, drip chambers D1, D2, D6 and D7 fitted with pressure gauges P1, P2, P6 and P7, as well as clamp valves V1, V9, V12, V13, V14 and V15 for performing ON/OFF and switching control over the flow channels. Also provided are infusers of physiological saline 221 for rinsing the circuits and recovering the residual blood, an infuser of anticoagulant heparin 208, a blood leak detector 209 for detecting the leakage of blood into the plasma emerging from the plasma separator, a blood warmer 210 for warming the returning blood to a specified temperature, an air bubble detector 211 for detecting the entrance of air bubbles into the returning blood, fluid shortage detectors 223, 224 for checking the supply of physiological saline and the replenishing fluid, and any other necessary devices.

The procedure of blood processing steps will now be outlined. Usually, the execution of blood treatment is preceded by the preparative steps of setting up the respective circuits and rinsing their interior with physiological saline. When the required preparation steps end, the blood pump 202 is started to run so that a blood sample is withdrawn into the collection circuit 201 through the collection tip and thence supplied into the plasma separator 204. The plasma separated from the blood in the plasma separator 204 is forced by means of the plasma exchange pump 226 to be discharged through the reject plasma channel 227. At the same time, the driving force provided by the plasma exchange pump 226 allows the replenishing fluid to be introduced into the replenishing supply channel 229 from the replenishing fluid supply means 213 in a volume equal to that of the discharged plasma. The introduced replenishing fluid is supplied into the return circuit 207 and returned to the patient after being combined with the blood permeate from the plasma separator 204.

The value of QPs which represents the target plasma flow rate for the plasma exchange pump 226 is given as a function of the blood pump flow rate QB and the pressure difference across the separation membrane TMP. In other words, the plasma exchange pump 226 is controlled to provide the target plasma flow rate QPs which is calculated at every moment based on the actual blood pump flow rate QB and the ratio determined from TMP.

In order to ensure that an abrupt load is not exerted on the separation membrane in the plasma separator 204 to cause an excessive pressure buildup, the initial acceleration $Vp_0$ for the plasma exchange pump 226 is usually set at a lower value than the normal acceleration $VP_1$. However, this is not always the case and depending on the specific situation of the treatment, $Vp_0$ may be set to be greater than $Vp_1$.

If the value of pressure TMP being monitored with the associated pressure sensor deviates from the limiting value to cause a pressure constraint, the plasma exchange pump flow rate QP is reduced at a specified deceleration $Vp_2$, which is set at a sufficiently great value to ensure that the pressure constraint can be removed rapidly. If the pressure constraint is removed, the plasma exchange pump flow rate QP is increased at the normal acceleration $Vp_1$ such that it is reverted toward the target plasma flow rate QPs.

Thus, in the present invention, if a pressure constraint is exerted on either pump whether it is the blood pump 202 or the plasma exchange pump 226, the pump flow rate is reduced at a comparatively large deceleration, thereby allowing for rapid elimination of the abnormal pressure state. During the restoration phase, the pump flow rate is increased mildly enough to avoid the excessive pressure buildup due to an abruptly increasing load and this enables the pumps to be operated with reduced occurrence of constraints.

If the plasma blood pump flow rate is to be reduced due to pressure constraints while the plasma exchange pump 226 is running normally, the exchange pump flow rate QP is reduced synchronously. In this case, the plasma exchange pump flow rate is determined on the basis of blood pump flow rate by the same technique as employed to calculate the target plasma flow rate QPs. It should, however, be noted that if the blood pump flow rate becomes lower than the prescribed value, the plasma exchange pump 226 is brought to a stop.

Figure 11A:
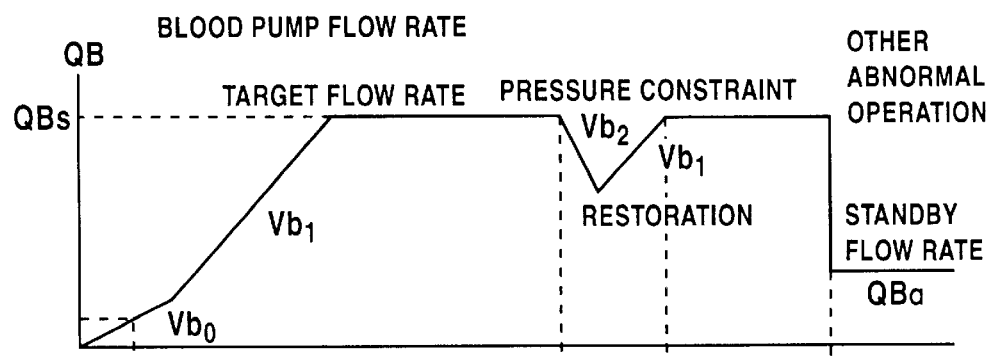
FIGS. 11A and 11B are graphs showing how various pumps are controlled in the blood treating method of the invention.
Figure 11B:
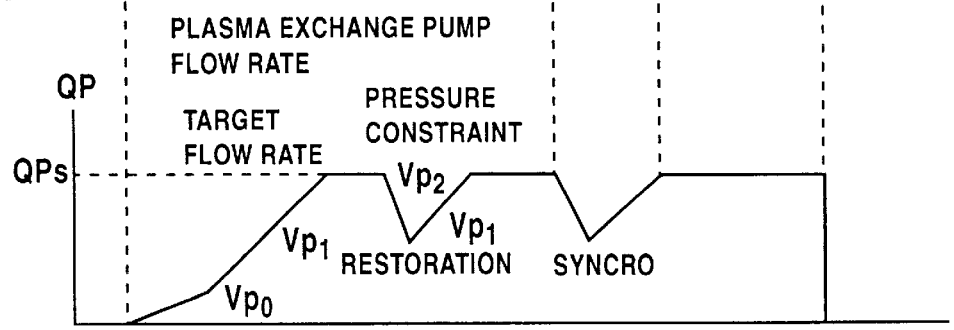

The above-described procedures of controlling the pumps are illustrated by timing charts in FIGS. 11A and 11B.

An example of the method of setting conditions for executing the blood treating steps by means of the blood processor shown in FIG. 10 will now be described below.

Immediately after the start of operation of the blood pump 202, the blood flow rate QB is increased at the initial acceleration $Vb_0$ which is set at an appropriate value within the range of 20 to 100 mL/min/min. when the integrated flow has reached 300 mL which is approximately equal to the sum of the capacities of the collection circuit 201 and the plasma separator 204, the initial acceleration $Vb_0$ is switched to the normal acceleration $Vb_1$ which is set at an appropriate value within the range of 20 to 150 mL/min/min and the blood pump flow rate is increased until the target blood flow rate QBs (=100 mL/min) is reached. The initial acceleration Vb is typically set to be smaller than the normal acceleration $Vb_1$ but this is not always the case of the invention. When the blood flow rate has reached the target value QBs, the operation of the blood pump 202 is controlled so as to maintain QBs.

The operation of the blood pump 202 is controlled in such a way that the monitored values of the blood collection pressure P1, the venous blood pressure P7 and the pressure difference across the plasma separator $\Delta P2/6$ will not exceed the limits of the respective values. If either one of said pressures deviates from the associated limiting value to cause a pressure constraint, namely, if P1 becomes lower than the lower limit, or if P7 exceeds the upper limit, or if $\Delta P2/6$ becomes greater than the upper limit, the blood pump flow rate QB is rapidly reduced at a sufficiently great deceleration of $Vb_2$ (=300 mL/min/min) to ensure that the pressure constraint is removed as soon as possible. When the pressure constraint is removed, the blood pump flow rate QB is increased again at the normal acceleration $Vb_1$ such that it is reverted toward the target blood flow rate QBs (=100 mL/min).

If there occurs any abnormality (as in valves) which is other than the pressure constraints while the blood pump is running normally, the blood pump flow rate QB is rapidly decelerated to the standby flow rate QBa ($\leq 50$ mL/min) which is preset by a blood flow rate setting device and the blood circulation is continued by controlling the blood pump 202 such as to maintain QBa. If the abnormal event under consideration is removed, QB is restored to the target value QBs. The procedure of executing the restoration to QBs has already been described above.

Referring now to the plasma exchange pump 226, it remains at rest until after the blood pump 202 has run to attain a QB value of 15 mL/min. When QB has reached 15 mL/min, the plasma exchange pump 226 is started to run. Until after the integrated plasma flow has reached 50 mL which is approximately equal to the volume of plasma on the secondary side of the plasma separator 204, the plasma exchange pump flow rate QP is increased at an initial acceleration of $Vp_0$ which is set within the range of 10 to 60 mL/min/min. Once the integral plasma flow has reached 50 mL, the plasma exchange pump flow rate QP is increased at a normal acceleration $Vp_1$ (10 to 100 mL/min/min) until it reaches the target plasma flow rate QPs. In order to ensure that the load on the machine parts will increase mildly, the normal acceleration $Vp_1$ is usually set to be greater than the initial acceleration $Vp_0$.

The plasma exchange 226 pump is controlled at every moment such as to maintain the target plasma flow rate QPs which is calculated on the basis of QB and TMP.

The target plasma flow rate QPs is expressed as QPs= K·R1·QB, where QB is the blood pump flow rate, K is a coefficient of plasma flow ratio which is preset by a plasma flow ratio setting device and R1 is a coefficient defined below on the basis of TMP:

R1=1.0−(TMP/upper limit of TMP)·(1.0−r)

where r is a coefficient of the upper limit of pressure difference and set at an appropriate value between 0.0 (inclusive) and 1.00 depending on the degree of internal plugging of the separation membrane. Depending on the properties of the blood to be treated and the quality of the separation membrane, the separation membrane occasionally has a great tendency to be plugged. If it is empirically known that the separation membrane is likely to be plugged, the value of r is set in the lower range. On the other hand, if it is empirically known that the separation membrane is free from the potential plugging, the value of r may be set in the higher range.

The coefficient of plasma flow ratio K is a parameter which is set by the plasma flow ratio setting device in consideration of the performance of the plasma separator and the properties of the blood to be treated and it is generally set within the range of 0.2 to 0.4, typically within the range of 0.25 to 0.35.

If TMP deviates from the limiting value, the plasma exchange pump flow rate QP is rapidly reduced at the specified deceleration $Vp_2$ (e.g., 140 mL/min/min). If the pressure constraint is eventually removed, QP is increased again at the normal acceleration $Vp_1$ so that it is reverted toward the target plasma flow rate QPs.

It should be noted that the limiting values of the various pressures to be monitored, namely, the lower limit of blood correction pressure P1, the upper limit of venous blood pressure P7, the upper limit of the pressure difference across the plasma separator $\Delta P2/6$ and the upper limit of the pressure difference across the separation membrane TMP, are each set to be a little lower than the threshold for the issuance of an alarm signal so as to assure safety in the treating operations. Specifically, a difference of about 20 mmHg is provided between the threshold and the respective limiting value.

The plasma exchange pump 226 is not operated independently of the blood pump 202 but the two pumps are controlled in operative association with each other. Even if the plasma exchange pump 226 is running normally, it may become necessary to reduce the blood pump flow rate QB on account of a pressure constraint; in that case, the plasma exchange pump flow rate QP is reduced synchronously such that the relation QP=K·R1·QB (for the definitions of K and R1, see above) is maintained at all times. If the blood pump flow rate QB is adjusted to be equal to the standby flow rate QBa when an abnormal event (as in valves) which is other than pressure constrains occurs, the plasma exchange pump 226 should, in principle, be brought to a stop.

In the embodiment under consideration, the plasma exchange pump 226 is so set that it will stop running if the blood pump flow rate QB falls below a certain value (e.g. 15 mL/min). It should, however, be noted that the lower limit of QB below which the plasma exchange pump 226 is brought to a stop is not necessarily 15 mL/min but may be determined as appropriate for parameters such as the performance of the pumps.

After the pressure constraints and other abnormal events are removed, the plasma exchange pump flow rate QP is restored and the procedure for the restoration is essentially the same as the already-described procedure for starting the operation of the plasma exchange pump 226.

According to the embodiment of the present invention, blood is processed in such a way that when the pressures being monitored by specified pressure sensors deviate from the respective limiting values to cause pressure constraints, various pump flow rates are reduced rapidly enough to ensure that the pressure constraints can be removed as soon as possible. After the pressure constraints are removed, the pump flow rates are restored at preset accelerations, again ensuring that there will be no excessive pressure buildups due to abruptly increasing loads.

If the blood pump flow rate is increased through two stages of acceleration when a blood sample is introduced immediately after the apparatus is started to operate, there will be no possibility of imposing an abrupt load on the apparatus and the target blood flow rate can be rapidly reached without causing a pressure buildup exceeding the limiting value. This is also true with the plasma exchange pump 226 and if its flow rate is increased through two stages of acceleration, the desired target plasma flow rate can be rapidly reached without causing a departure from the limiting value of pressure.

If any abnormal event other than pressure constraints occurs while the blood pump 202 is operating normally, the blood pump 202 is controlled in such a way that its flow rate is decelerated rapidly while a standby flow rate is maintained at a value not exceeding a preset upper limit; this ensures safety in the blood treatment without stopping its flow, thereby preventing the blood from being coagulated in the circuits.

If the plasma pump flow rate is controlled as a function of the pressure difference across the separation membrane in the plasma separator 204, it can be set at an optimal value reflecting the degree of plugging of the separation membrane which is variable at every moment. As a result, the progress of the plugging of the separation membrane can be retarded and the required blood treatment can be accomplished without being interrupted or undergoing some constraints.

What is claimed is:

1. An apparatus for blood treatment comprising
    a collection circuit which includes a blood pump and into which a blood sample is withdrawn by means of said blood pump,
    a treatment circuit for performing a treatment on the withdrawn blood sample, and
    a return circuit through which the treated blood sample is returned to the patient,
    pressure gauges provided in at least one circuit among the collection circuit, the treatment circuit and the return circuit, and
    means for controlling the operation of the blood pump by
        (i) from the start of the treatment, increasing a flow rate of said blood pump at a preset normal acceleration until a specified target blood flow rate is reached,
        (ii) once said target blood flow rate has been reached, operating said blood pump so as to maintain said target blood flow rate,
        (iii) reducing said flow rate of said blood pump at a specified deceleration if values of pressure detected by specified pressure gauges among said pressure gauges or values calculated on the basis of said pressure values deviate from respective limiting values to cause pressure constraints during operation of said blood pump to (a) increase said flow rate of said blood pump at said preset normal acceleration or (b) maintain said flow rate of said blood pump at said target blood flow rate, and
        (iv) if said pressure constraints are removed, increasing said flow rate of said blood pump at said normal acceleration so that it is reverted to said target blood flow rate,
    wherein
    the treatment circuit includes an adsorptive blood treatment circuit which includes a plasma separator, a plasma pump and an adsorber, and in which a plasma separated from the blood sample by means of said plasma separator is directed by said plasma pump into said adsorber where unnecessary components are removed from the plasma, and
    said apparatus further comprises means for controlling the operation of said plasma pump by
        (i) starting said plasma pump after said blood pump rate exceeds a predetermined value,
        (ii) increasing a flow rate of said plasma pump at a preset normal acceleration after the start of said plasma pump and until a specified target plasma flow rate calculated based on said flow rate of said blood pump is reached,
        (iii) controlling the operation of said plasma pump so as to maintain said target plasma flow rate once it has been reached,
        (iv) reducing said flow rate of said plasma pump at a specified deceleration if values of pressure detected by the specified pressure gauges or values calculated on the basis of said pressure values deviate from respective limiting values to cause pressure constraints, and
        (v) increasing said flow rate of said plasma pump at said normal acceleration so that it is reverted toward said target plasma flow rate if said pressure constraints are removed.

* * * * *